(12) United States Patent
Abdoli-Eramaki

(10) Patent No.: US 7,553,266 B2
(45) Date of Patent: Jun. 30, 2009

(54) LIFT ASSIST DEVICE AND METHOD

(75) Inventor: Mohammad Abdoli-Eramaki, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 414 days.

(21) Appl. No.: 11/011,048

(22) Filed: Dec. 15, 2004

(65) Prior Publication Data

US 2005/0130815 A1 Jun. 16, 2005

Related U.S. Application Data

(60) Provisional application No. 60/529,111, filed on Dec. 15, 2003.

(51) Int. Cl.
 A63B 21/02 (2006.01)
 A61F 5/00 (2006.01)
(52) U.S. Cl. .................................. 482/124; 602/19
(58) Field of Classification Search ................ 482/124; 602/19, 32, 36; 606/241
See application file for complete search history.

(56) References Cited

U.S. PATENT DOCUMENTS

| | | | | |
|---|---|---|---|---|
| 654,173 A | * | 7/1900 | Mendenhall | 2/44 |
| 1,202,851 A | * | 10/1916 | Kelly | 2/44 |
| 1,409,326 A | * | 3/1922 | Williamson | 2/44 |
| 1,544,162 A | * | 6/1925 | La Vigne | 2/44 |
| 2,358,551 A | | 9/1944 | Beaton | |
| 2,906,260 A | | 9/1959 | Myers | |
| 3,570,011 A | * | 3/1971 | Naig | 2/44 |
| 4,553,551 A | | 11/1985 | Gross | |
| 4,773,106 A | | 9/1988 | Toso et al. | |
| 4,813,080 A | | 3/1989 | Toso | |
| 4,829,989 A | * | 5/1989 | Deamer et al. | 602/19 |

(Continued)

FOREIGN PATENT DOCUMENTS

AU 199929119 B2 9/1999

(Continued)

OTHER PUBLICATIONS

Barett, A.L., et al., "Evaluation of four weight transfer devices for reducing loads on the lower back during agricultural stoop labour." 2001 ASAE Annual International Meeting, Jul. 30-Aug, 1, 2001.

(Continued)

*Primary Examiner*—Fenn C Mathew
(74) *Attorney, Agent, or Firm*—Stephen J. Scribner; Angela Lyon; Carol Miernicki Steeg

(57) ABSTRACT

The invention relates to a device and method for assisting a subject to perform a motion such as a lift. The invention comprises a first anchor attachable to a first side of a joint of the subject's body, a second anchor attachable to a second side of the joint; and an elastic member connecting the first anchor and the second anchor, such that articulation of the joint in a first direction causes deformation of the elastic member and storing of energy, and articulation of the joint in a second direction causes relaxation of the elastic member wherein the energy is released and assists the subject to perform a motion in said second direction. The invention may be used at a subject's waist, ankle, wrist, knee, hip, elbow, shoulder, and/or at least one joint of the back and/or neck.

8 Claims, 13 Drawing Sheets

U.S. PATENT DOCUMENTS

| | | | |
|---|---|---|---|
| 5,001,791 A | | 3/1991 | Toso |
| 5,016,869 A | * | 5/1991 | Dick et al. ............... 482/75 |
| 5,083,554 A | | 1/1992 | Toso |
| 5,176,622 A | * | 1/1993 | Anderson et al. ........... 602/19 |
| 5,209,716 A | | 5/1993 | Frydman et al. |
| 5,235,714 A | | 8/1993 | Toso |
| 5,375,279 A | | 12/1994 | Toso |
| 5,643,184 A | | 7/1997 | Toso |
| 5,860,944 A | | 1/1999 | Hoffman, Jr. |
| 5,951,591 A | * | 9/1999 | Roberts .................. 606/241 |
| 6,129,691 A | | 10/2000 | Ruppert |
| 6,436,065 B1 | * | 8/2002 | Mitchell ................... 602/19 |
| 6,450,131 B1 | | 9/2002 | Broman |

FOREIGN PATENT DOCUMENTS

| | | |
|---|---|---|
| CA | 2119760 | 4/1993 |
| WO | WO 99/45863 A1 | 9/1999 |

OTHER PUBLICATIONS

Deamer, R.M., et al., "Technical forum: imporved orthotic lower-back support for help with low-back pain." Journal of Prosthetics & Orthotics, 9: 38-41 (1997).

Handasyde, L.E., "Bendezy benefits bad backs—brilliant & unique invention!!" http://www.greataustralian.com/content.php?page_id=37&menu=210106.

Fathallah, F.A., et al., "Stooped and squatting postures in the workplace." Conference Proceedings, Center for Occupational and Environmental Health, Oakland, California, Jul. 29-30, 2004.

Cholewicki, J., "The effects of lumbosacral orthoses on spine stability: What changes in EMG can be expected?" Journal of Orthopaedic Research 22: 1150-1155 (2004).

Kawai, S., et al., "Development of a small size controller for control of wearable power assist device." The Fourth International Conference on the Advanced Mechatronics (ICAM) pp. 407-412 (2004).

Kawai, S., et al., "An analysis of human motion for control of a wearable power assist system." Journal of Robotics and Mechatronics 16: 1-8 (2004).

Kawai, S., et al., "A study for control of a power assist device—development of an EMG based controller considering a human model." Proceedings of IEEE/RSJ International Conference on Intelligent Robots and Systems, Sendai, Japan pp. 2283-2288 (2004).

Kawai, S., et al., "A study for control of a wearable power assist system—recognition of human motions by surface EMG signals." Proceedigns of IEEE/RSJ International Conferene on Intelligent Robots and Systems, Sendai, Japan pp. 1-6 (2004).

Naruse, K., et al., "Design of compact and lightweight wearable power assist device." Proceedings of IMECE '03 2003 ASME International Mechanical Engineering Congress and Exposition, Washington, D.C., U.S.A., pp. 1-8, Nov. 2003.

Naruse, K., et al., "Development of wearable exoskeleton power assist system for lower back support." Proceedings of the IEEE/RSJ International Conference on Intelligent Robots and Systems, Las Vegas, Nevada, U.S.A., pp. 3630-3635, Oct. 2003.

\* cited by examiner

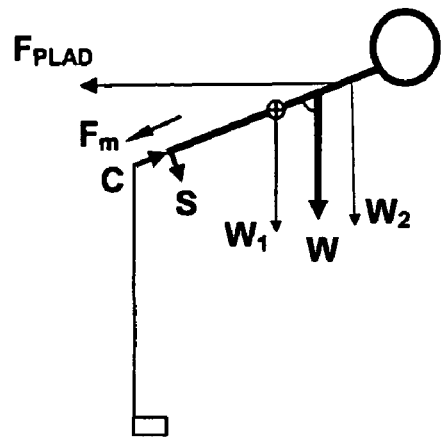
Figure 5
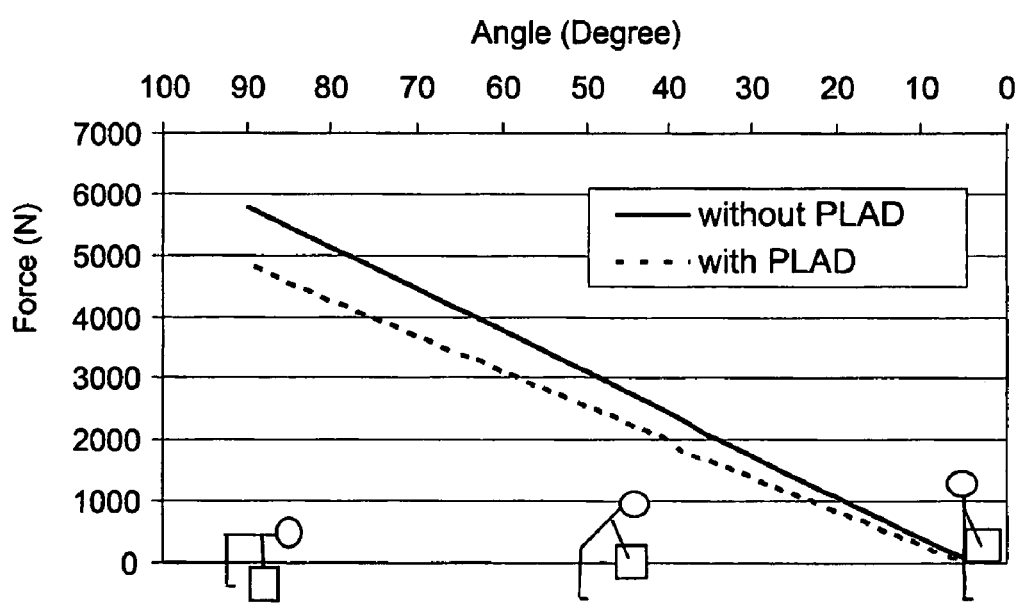
Figure 6

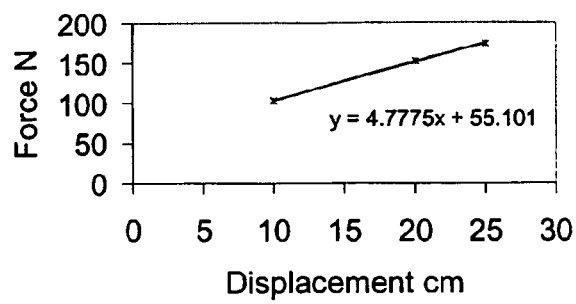
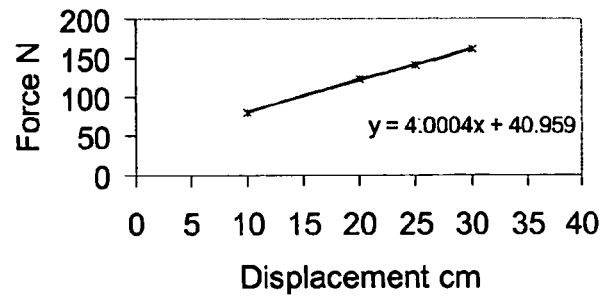
Figure 9(a)  Figure 9(b)
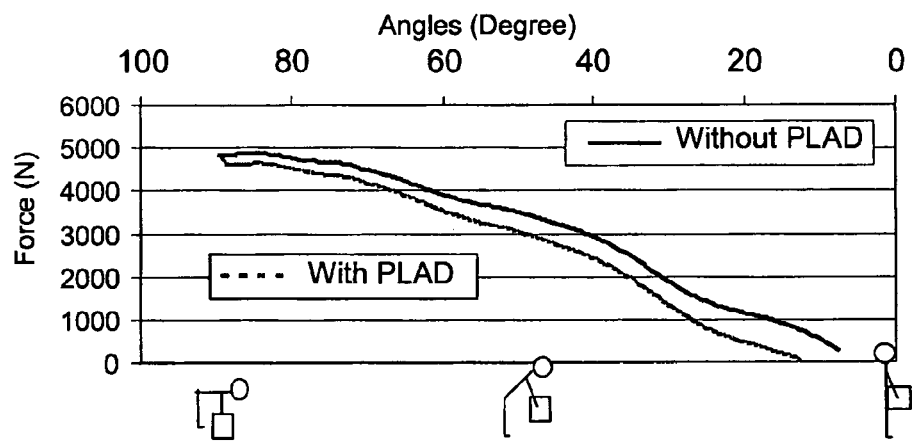
Figure 10

LIFT ASSIST DEVICE AND METHOD

RELATED APPLICATIONS

This application claims the benefit of the filing date of U.S. Provisional Patent Application No. 60/529,111, filed Dec. 15, 2003, the contents of which are incorporated herein by reference in their entirety.

FIELD OF THE INVENTION

The invention relates to a motion assistance device that is worn by a subject, and which stores and provides energy for aiding a task or motion involving articulation of one or more joints, particularly lifting or moving a mass. In particular, the invention provides a device and method for assisting a subject to perform a manual task such as lifting an object.

BACKGROUND OF THE INVENTION

During bending and lifting activities, erector spinae muscles must generate a large extensor moment to raise the upper body, and the object lifted, into an upright position (McGill and Norman, 1986). Since these muscles act on short lever arms, a high tensile force is required, and the lumbar intervertebral discs are subjected to a high compressive force. Occupations and tasks which demand frequent and heavy lifting are associated with a greatly increased risk of disc prolapses (Kelsey et al., 1984) and with low back pain in general (Kelsey and White, 1980). Indeed, severe chronic or acute low back injuries account for 25% of workers' compensation claims in the U.S. (Guo et al, 1995).

Injury prevention strategies include educating workers regarding proper techniques for lifting, sharing lifting tasks between several workers, and using mechanical aids for lifting (Waters and Putz-Andersson, 1994). Mechanical lifting devices, such as hoists, are effective in eliminating muscle strain when loads are beyond human lifting capability. However, when loads are within perceived human lifting capability, there is a tendency for subjects to lift manually as most mechanical lifting aids are slower than human speed and may not be easily accessible (Kazerooni, 2002).

Devices that are worn and support subjects in performing lifts have been proposed. An example of such a device is a lifting belt which acts as a rigid band around the waist, thus increasing intra-abdominal pressure. Current research findings suggest that lifting belts are not an effective means of reducing spinal loads (McGill, 1993 and 2002; NIOSH, 1994; Lavender et al., 2000; Chen, 2003), but might enhance spinal stability (Cholewicki, 2004; Hodges et al., 2004). However, it has been shown that wearing a lifting belt increases blood pressure which may increase the incidence of hemorrhoids, hernias, and varicose veins, particularly testicular varicose veins (Harman et al., 1989; Rafacz and McGill, 1996).

There is a need for an affordable effective device which is comfortably worn and helps a subject to perform activities that can otherwise lead to muscle strain.

SUMMARY OF THE INVENTION

In a first aspect of the invention there is provided a device for assisting a subject to perform a motion, comprising: a first anchor attachable to a first segment on a first side of one or more joints of the subject's body; a second anchor attachable to a second segment on a second side of the one or more joints; and an elastic member connecting the first anchor and the second anchor; wherein when said first and second anchors are attached to the first and second segments, articulation of the one or more joints in a first direction causes deformation of the elastic member and storing of energy, and articulation of the one or more joints in a second direction causes relaxation of the elastic member and release of stored energy; and wherein the release of stored energy assists the subject to perform a motion in said second direction.

In one embodiment, wherein tension of the elastic member is adjustable. The elastic member may be selected from a spring, an air-, liquid-, or gas-filled actuator, a magnetic actuator, an elastic band, tube, or cord, and a combination thereof. In another embodiment, at least one of the anchors may be fixed to clothing. The one or more joints may be selected from the group consisting of waist, ankle, wrist, knee, hip, elbow, shoulder, and at least one joint of the back and/or neck. The first and second anchors may be independently selected from a bar, ring, clip, hook, buckle, roller, pulley, guide, channel, and a receptacle.

In another embodiment, the invention further comprises: a first belt for attaching to the first segment; and a second belt for attaching to the second segment; wherein the first and second anchors are disposed on the first and second belts.

According to another aspect of the invention, there is provided a device for assisting a subject to perform a lift, comprising: a first anchor attachable to the subject's shoulder; a second anchor attachable to the subject's waist; at least a third anchor attachable to at least one of the subject's legs; a first elastic member connecting the first anchor and a second anchor; and a second elastic member connecting the second anchor and the at least third anchor; wherein, when the first and second elastic members are attached to the first, second, and third anchors, upon articulation of at least one joint selected from (a) one or more joints of the back, (b) the waist, and (c) the knee(s), at least one of said first and second elastic members is deformed or relaxed.

In one embodiment, tension of at least one of the first and second elastic members is adjustable. In other embodiments, at least one of said anchors may be fixed to clothing, and the first and second elastic members may be independently selected from a spring, an air-, liquid-, or gas-filled actuator, a magnetic actuator, an elastic band, tube, or cord, and a combination thereof. The first, second, and third anchors may be independently selected from a bar, ring, clip, hook, buckle, roller, pulley, guide, channel, and a receptacle.

In another embodiment, the device may further comprise: a first belt for attaching to the subject's shoulders; a second belt for attaching to the subject's waist; and a pair of leg belts for attaching to the subject's legs; wherein the first and second anchors are disposed on the first and second belts, and the third anchor comprises a pair of anchors, a first anchor of the pair being disposed on one of the leg belts, and a second anchor of the pair being disposed on a second leg belt.

In accordance with another aspect of the invention there is provided a method for assisting a subject to perform a motion, comprising: attaching a first anchor to a first segment on a first side of one or more joints of the subject's body; attaching a second anchor to a second segment on a second side of the one or more joints; and connecting an elastic member between the first anchor and the second anchor; wherein articulation of the one or more joints in a first direction causes deformation of the elastic member and storing of energy, and articulation of the one or more joints in a second direction causes relaxation of the elastic member and release of stored energy; and wherein the release of stored energy assists the subject to perform a motion in said second direction.

A further aspect of the invention relates to a method for assisting a subject to perform a lift, comprising: attaching a first anchor to the subject's shoulder; attaching a second anchor to the subject's waist; attaching at least one anchor to at least one of the subject's legs; connecting a first elastic member between the first anchor and the second anchor; and connecting a second elastic member between the second anchor and the anchor(s) attached to at least one of the subject's legs; wherein, upon articulation of at least one joint selected from (a) one or more joints of the back, (b) the waist, and (c) the knee(s), at least one of said first and second elastic members is deformed or relaxed; and wherein deforming and relaxing of the elastic member assists the subject in performing a lift.

In another aspect, the invention provides a device for assisting a subject to perform a motion, comprising: a first anchor attachable to a first segment on a first side of one or more joints of the subject's body; a second anchor attachable to a second segment on a second side of the one or more joints; and an electric motor and cable connected to the first anchor and the second anchor; wherein when said first and second anchors are attached to the first and second segments, the electric motor senses articulation of the one or more joints and controls tension in the cable; wherein controlling tension in the cable assists the subject to perform the motion.

In one embodiment, the device may further comprise: a third anchor attachable to a third segment on a first or second side of the one or more joints; and at least one electric motor and cable connected to at least one of (a) the first anchor and the second anchor, (b) the second anchor and the third anchor, and (c) the first anchor and the third anchor; wherein when said first, second, and third anchors are attached to the first, second, and third segments, the at least one electric motor senses articulation of the one or more joints and controls tension in the cable; and wherein controlling tension in the cable assists the subject to perform the motion.

In a another aspect of the invention there is provided a device for assisting a subject to perform a motion, comprising a first anchor attachable to a first side of a joint of the subject's body, a second anchor attachable to a second side of the joint; and an elastic member connecting the first anchor and the second anchor such that when said first and second anchors are attached, articulation of the joint in a first direction causes stretching of the elastic member and storing of energy, and articulation of the joint in a second direction causes relaxation of the elastic member wherein the energy is released and assists the subject to perform a motion in the second direction.

In another aspect, the invention provides a device for assisting a subject to perform a lift comprising a first anchor attachable to the subject's shoulder, a second anchor attachable to the subject's lower back, a third anchor attachable to the subject's lower leg, a first elastic member connecting the first anchor and the second anchor, and a second elastic member connecting the second anchor and the third anchor; such that upon articulation of the subject's upper back at least one of the first and second elastic members is stretched or relaxed.

In a further aspect, the invention provides a device for supporting a portion of a subject's body, comprising a first anchor attachable to a portion of the subject's body, a second anchor attachable to a stationary object, and an elastic member connecting the first anchor and a second anchor; such that when said first and second anchors are attached, upon articulation of the body portion the elastic member is stretched or relaxed.

In a further aspect of the invention, thee invention provides a method for assisting a subject to perform a motion comprising attaching a first anchor to a first side of a joint of the subject's body, attaching a second anchor to a second side of the joint, and connecting an elastic member between the first anchor and the second anchor; such that articulation of the joint in a first direction causes stretching of the elastic member and storing of energy, and articulation of the joint in a second direction causes relaxation of the elastic member wherein the energy is released and assists the subject to perform a motion in the second direction.

In another aspect, the invention provides a method for assisting a subject to perform a lift comprising attaching a first anchor to the subject's shoulder belt, attaching a second anchor to the subject's lower back, attaching a third anchor to the subject's lower leg, connecting a first elastic member between the first anchor and the second anchor, and connecting a second elastic member between the second anchor and the third anchor; such that upon articulation of the upper back at least one of the first and second elastic members is stretched or relaxed.

In another aspect, the invention provides a method for supporting a portion of a subject's body, comprising attaching a first anchor to a portion of the subject's body, attaching a second anchor to a stationary object, and connecting an elastic member between the first anchor and the second anchor; such that upon articulation of said portion of the subject's body the elastic member is stretched or relaxed.

In another aspect of the invention, tension of the elastic members may be adjustable. The anchors may be fixed to clothing. The invention also provides a kit comprising attachable anchors and elastic members. In some embodiments of the kit the anchors are fixed to clothing. In some embodiments the elastic members are adjustable. The anchors may comprise a loop, ring, clip, buckle or hole. In further aspects of the invention, the elastic member may be a spring, a pneumatic actuator, or a member made of an elastic material. The joint may be the waist, ankle, wrist, knee, hip, elbow, shoulder and at least one joint of the back or neck.

In some embodiments, the invention may be configured to provide energy to the legs, to assist a subject in performing a motion such as walking or climbing stairs. Such an embodiment may comprise only the bottom portion of the device shown in FIG. 1, with the same or different arrangement of elastic members connected between anchors at the waist and at the lower legs and/or feet.

BRIEF DESCRIPTION OF THE DRAWINGS

Embodiments of the invention will now be described, by way of example, with reference to the accompanying drawings, wherein:

FIG. 5 is a diagram depicting the direction of mechanical vectors of a subject in a stoop position when PLAD is worn;

FIG. 6 is a graph showing the calculated resultant force exerted by erector spinae muscles of a subject lifting a 10 kg object with and without PLAD;

FIGS. 9(a) and (b) are graphs showing the force required to deform specific elastic members that could be used in the (a) lower and (b) upper body portions of PLAD;

FIG. 10 is a graph showing modeled resultant force exerted by erector spinae muscles of a subject lifting a 10 kg object with and without PLAD;

DETAILED DESCRIPTION OF PREFERRED EMBODIMENTS

Figure 1:
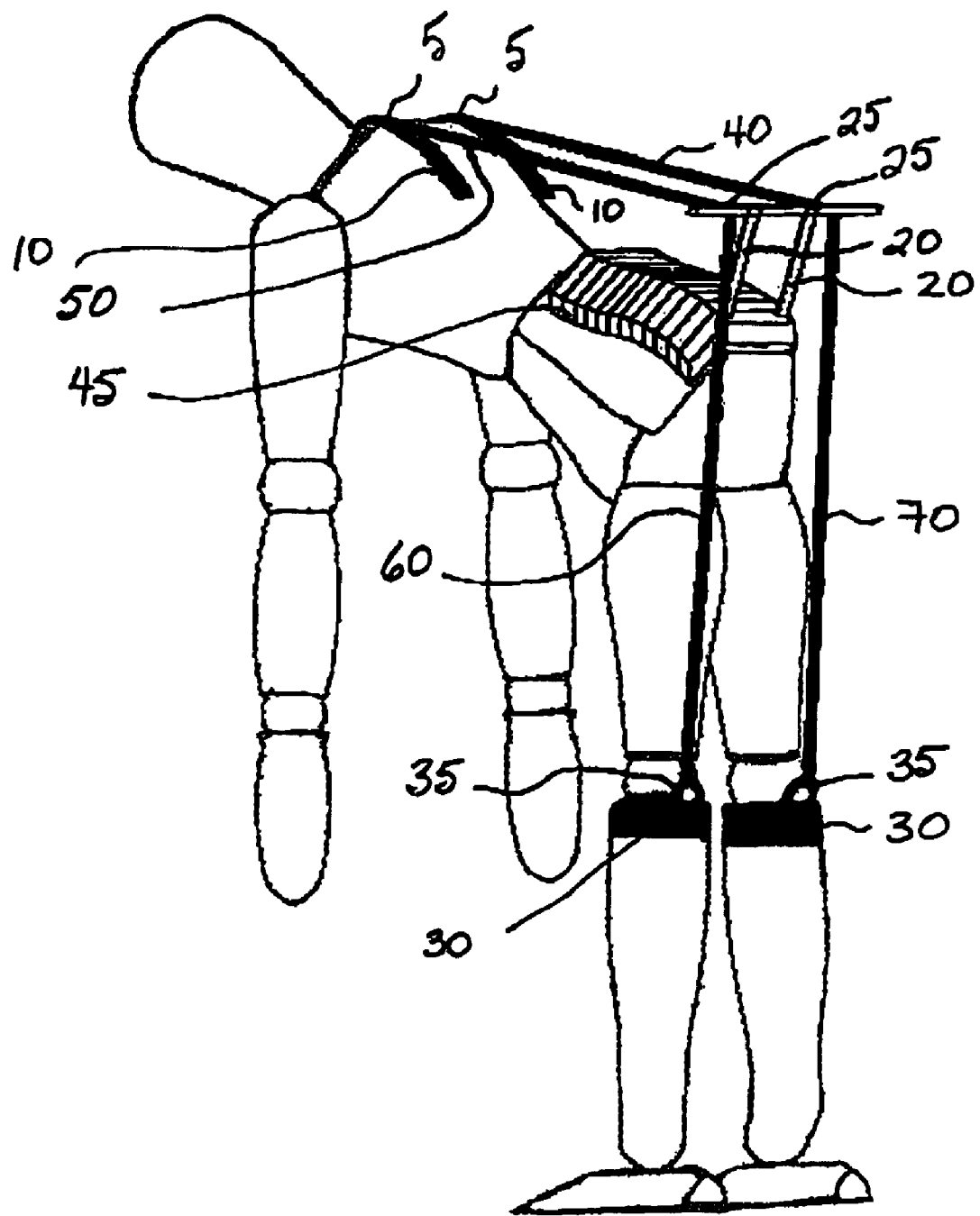
FIG. 1 is a drawing of a preferred embodiment of the invention, referred to herein as a Personal Lift Assist Device (PLAD), wherein anchors are placed at the shoulders, below the knees, and at the lower back of a subject, and elastic members are connected between the anchors.

The invention provides a motion assistance device that is worn by a subject, and which stores and provides energy for aiding a task or motion involving articulation of one or more of the subject's joints. The invention further provides a method for assisting a subject to perform a motion. The motion can be, e.g., lifting an object. The device of the invention can be used, for example, for lifts and/or for repetitive tasks that may lead to muscle strain and/or for statically held postures. The invention provides at least one elastic member connecting two body points on opposite sides of one or more joints, such that articulation of the joint(s) in a first direction leads to stretching or deformation of the elastic member, and storing of energy, and articulation of the joint(s) in a second (usually opposite) direction leads to relaxation of the elastic member and releasing of energy. In this way, energy is stored and provided to the body during articulation of the joint in the direction of relaxation of the elastic member.

As used herein, the term "elastic member" means a member which can be deformed (and thereby energized), and relaxed. The term "deformed" means reversibly bent, stretched, or compressed such that energy is stored in the elastic member. The term "relaxed" means the original (undeformed) state of the elastic member prior to being deformed. Preferably, when deformed and then allowed to relax, the elastic member returns substantially to its original undeformed state and energy stored in the elastic member is thereby released. Examples of elastic members may include, but are not limited to: springs, for example, leaf, spiral, helical, or coil springs; air-, liquid-, or gas-filled actuators, or magnetic actuators; and elastic materials, for example, elastic bands or tubes made of rubber or any natural or synthetic materials; and combinations thereof. For example, an elastic member may comprise a "bungee" cord, or an elastic band available from Thera-Band® (Akron, Ohio) or FlexBand®) (Stow, Ohio). Elastic members may be provided as single units or as combinations of units. For example, elastic members may comprise single or multiple elastic bands, the latter comprising parallel, crossed, braided, etc. elastic bands. According to the invention, energy released upon relaxation of the elastic member may aid in performing certain tasks by supplementing muscles, preventing muscle strain and/or disc injury. The invention may also be used to supplement weak or tired muscles, for example, to prevent back pain or to aid recovery from a back injury.

The invention provides an elastic member in a manner that assists one or more muscles during lifting/bending motions. For example, an elastic member may be aligned parallel to the extensor and/or flexor muscles of a joint of a subject. The term "extensor" refers to a muscle, the contraction of which causes articulation at a joint with the consequence that the associated limb or body part assumes a more straight line, or so that the distance between the body segments on either side of the joint is increased or extended. The term "flexor" refers to a muscle, the contraction of which causes articulation of a joint so as to bring together the two body segments which it connects. The term "segment" refers to a part of the body on one side of a joint. For example, the body segment directly above the knee joint is the upper leg, and the body segment directly below the knee joint is the lower leg. Examples of joints that the invention can assist include, but are not limited to, wrist, waist, ankle, knee, hip, elbow, shoulder, and one or more joints of the back or neck. Although not limited thereto, the invention is particularly suitable for aiding subjects during lifting tasks. While many trunk muscles are involved in lifting tasks, the erector spinae (columns of muscles running the length of the human spine which insert into ribs and vertebrae) are muscles of critical importance. During bending and lifting activities, the erector spinae must generate a large extensor moment to raise the upper body, and the object lifted, into an upright position (McGill and Norman, 1986). Since the erector spinae muscles act on a short lever arm, a high tensile force is required, and the lumbar intervertebral discs are subjected to a high compressive reaction force.

According to a preferred embodiment, the invention provides a device for assisting a subject during forward- or side-leaning and/or during a lifting task. In such embodiment, referred to herein as a personal lift assist device or "PLAD", the device comprises an elastic member that assists the erector spinae muscles of the back. The elastic member connects to the body at the shoulders or upper trunk, and at least one of the waist, lower legs, or the feet. This connection leads to transfer of some of the forces and moments from a subject's spinal column to his/her shoulders, waist, and lower leg. The term "waist" means the lower back at or about the hip or belt line and includes the pelvic girdle. Thus, articulation of the waist refers to articulation of all joints between and including the L4/L5 vertebrae to the pelvic girdle.

This embodiment transfers compression force from the upper body to the lower body. It relies on the subject's hip to act as a fulcrum and transfers the weight of the upper torso to the lower leg at either the level of the feet or of the leg's tibial tuberosity. The feet are able to bear enormous body weight and are well suited to receive this transfer of weight. The tibial tuberosity is a strong bony plateau below the knee which is the site of attachment of the quadriceps muscles, and it also bears the body weight of people with prosthetic devices for below-knee amputations. The hip level force of this embodiment acts on the pelvic girdle, and not the lumbar vertebrae. The pelvic girdle is a solid bony structure that is well adapted to receiving force. Typical magnitudes of point forces generated by this embodiment range from 125 N to 325 N. These forces, when spread evenly across the back of the pelvis, are well within the compressive strength characteristics of bone (Hobson, 1992).

The preferred embodiment also reduces some of the force requirements needed by the hip extensors (gluteal muscles and hamstring muscles) and knee extensors (quadricep muscles). As a subject wearing PLAD lowers his/her body, the elastic member is deformed (stretched). This stretch provides stores energy to assist with extension of the hips and knees during the upward phase of a lift. This assistance provided by PLAD can be modelled mathematically and demonstrated by monitoring the level of electrical activity of the muscles (electromyography) of subjects performing lifts with and without PLAD (see below examples).

An example of such a preferred embodiment is depicted in FIG. 1, and comprises an adjustable shoulder belt 10, an adjustable waist belt 45, and two adjustable leg belts 30. The term "belt" is used herein to refer to a harness that comfortably and securely attaches to subject's body, and may include one or more adjustable straps, optionally with padding, with fasteners such as buckles, that encompass the body in the area of the shoulder(s), waist, or leg(s), as required. Each belt has an anchor for connecting one or more elastic members thereto. The term "anchor" refers to a locus to which an elastic member may be securely attached, or through which an elastic member may pass. An anchor may comprise, for example, a bar, a ring, a clip, a hook, a buckle, a roller, a pulley, a guide, a channel, or a receptacle, or the like, or a combination thereof. The term "receptacle" refers to any suitable means adapted for receiving a coupling or connector, or an orifice through which an elastic member may be inserted, looped, or tied. For example, as shown in FIG. 1, two elastic members 40, 50 may be connected between the shoulder 10 and waist 45 belts, and two additional elastic members 60, 70 may be connected between the waist 45 and leg 30 belts, in substantially parallel arrangements, using shoulder, waist, and leg anchors 5, 25, and 35, respectively. Alternatively, for example, the two elastic members connected between the shoulder and waist belt anchors may be connected in crossed arrangement, in an "X" formation (not shown in FIG. 1). In another embodiment, elastic members may be connected between the shoulder and waist belt anchors in both substantially parallel and crossed arrangement (not shown in FIG. 1). In yet another embodiment, one or more continuous elastic members may be connected from the shoulder anchors to the leg anchors, passing over or through the waist anchors. In such embodiment, the waist anchors maybe configured as guides, so as not to constrain sliding and stretching of the elastic member.

Suitable lengths of elastic members may be selected for each subject. For example, when a subject is wearing the PLAD, the length of each elastic member is adjusted so as to have some slack (i.e., no tension) when the subject is standing upright and to be taut when the subject is bent forward at approximately 10° from vertical.

Suitable strength or resistance (i.e., the force required to deform the elastic member by a given amount) of elastic member may be determined by one or more of the following. An empirical approach may be used wherein various strengths of elastic member are tried until a subject finds the preferred strength for a given task, and/or an elastic member strength that is comfortable. A selection procedure may also involve consideration of selection criteria, including any of a subject's body weight, upper body weight (defined as the weight of the body above the L5 vertebra; for 75% of the adult population, this is equal to about 55% of total body weight), body size, body strength, and the weight of the object being lifted. Analyses currently in progress are aimed at elucidating the appropriate selection criteria. Elastic bands and tubing such as those made by Thera-Band® are available in various colour-coded levels of strength, selection of which is expected to be straight-forward upon identification of the appropriate selection criteria.

As shown in FIG. 1 and briefly discussed above, in a preferred embodiment of PLAD, anchors 5 are disposed on the shoulder belt 10 at each shoulder, anchors 25 are disposed on the waist belt 45, and anchors 35 are disposed on the lower-leg belts 30. The anchors secure one or more elastic members 40, 50, 60, 70, which are strung between them. In FIG. 1, anchor 35 is depicted as a ring while anchor 25 is depicted as a bar around which elastic members 40, 50, 60 and 70 may be looped. The anchor or anchors associated with a belt may be mounted in such a way that they are elevated from the belt and hence elevated from that point on the subject's body. For example, as shown in FIG. 1, the bar comprising anchor 25 associated with the waist belt is elevated from the belt a distance "a", using a spacer or standoff 20. This creates or increases a fulcrum for the elastic members attached thereto. In other embodiments, waist, shoulder, and/or leg belts, or belts for other body segments, may similarly employ such a fulcrum.

When a subject wearing PLAD bends his/her upper body (i.e., the portion of the body above the L4 vertebra) forward or sideways, the elastic members are stretched and thus support a portion of the weight of the upper body at all angles greater than, for example, 10 from vertical. Following the bend, the subject may resume an upright stance, assisted by release of energy from the elastic members. If the subject is also lifting an object, then the lift is also assisted since while resuming an upright stance, energy is released from the elastic members and decreases the demands on the back muscles.

In the preferred embodiment, the elastic member is stretched by bending of the body and relaxed by upward straightening of the body. The subject uses the force of gravity acting on his/her upper body, particularly when it is several degrees or more from vertical, to aid in stretching the elastic member and storing energy. The subject then gains energy from the elastic member while straightening the back, which may or may not include lifting an object.

In another embodiment of PLAD, an elastic member is strung between the shoulder, waist, and/or lower leg belts with sufficient tension to assist a subject to hold a static leaning position, such as forward-leaning. The static stretch of the elastic member is used to counterbalance the holding of a lift, or the maintaining of a forward-leaning stance. In this embodiment, a large force would be required to further stretch or deform the elastic member after the subject has reached the equilibrium point of the lean, at a desired angle from vertical. In this manner, a body part's weight with or without a lifted object's weight can be counterbalanced by the energy stored in the elastic member. Thus, the body part, or body part with lifted object, is held in static equilibrium with little to no muscle force needed to counterbalance the weight. By this mechanism, the muscles are able to relax during the static holding task. In a related embodiment of the invention, tension in one or more elastic members may be adjusted so that the subject can obtain the maximum comfort and benefit. Such an embodiment could support a leaning subject's upper body weight, thereby preventing muscle fatigue if the subject maintains that position for an extended amount of time. Examples of professions which might require prolonged forward leaning include dental assistant, surgeon, and assembly line worker.

With the PLAD embodiment, the amount of muscular force required of the erector spinae is reduced lumbar moments, compressive forces, and shear forces during bending and/or lifting are reduced. Furthermore, these reductions reduce the likelihood of lower back pain caused by, for example, repetitive bending and/or lifting.

Detailed calculations of forces and moments produced during bending and lifting, with and without PLAD, including an assessment of the forces transferred to other body parts, and a comparison of erector spinae electromyography with and without PLAD, are presented in the examples below. Evidence shows that PLAD reduces the moment, compressive, and shear forces on the disc between the L4 and L5 vertebrae as well as the amount of work required of the erector spinae muscles.

A second embodiment of the invention (see FIG. 2) provides additional support for side-leaning or lifting in a twisted position when compared to PLAD. In this embodiment of the invention, an additional elastic member 65 is attached to an anchor 80 disposed on the side of the waist belt 45 and to an anchor 75 disposed on a side portion 85 of the shoulder belt 10. The leg belt 30 has a tibial tuberosity anchor 35, and an additional elastic member 55 is looped under the foot. This combination allows the weight of the upper body to be transferred to both the tibia and the foot.

A third embodiment of the invention provides support of the upper body while leaning forward or sideways in a sitting position. In this embodiment, an elastic member is fixed to a subject's upper body (e.g., using a shoulder belt) and to a stationary object, for example, a piece of furniture such as a chair. With proper positioning and tension of the elastic member, the weight of the upper body can be supported by the elastic member as the subject leans forward or sideways. Examples of professions which might require prolonged forward-leaning in a sitting position include jeweler and microchip technician.

A fourth embodiment of the invention incorporates an elastic member into clothing such as overalls. According to this embodiment, anchors are fixed, for example, sewn-in, to clothing and the elastic members may pass through channels sewn-in to the clothing, which allow the elastic members to stretch while holding them in place. Elastic members may be anchored at intermediate points to accommodate different ranges of motion of particular body parts. Clothing may include stirrups that go under the feet, or built-in socks or shoes that have an integrated loop which passes under the foot, to anchor the elastic member (see FIG. 2). Such an embodiment may be provided in different sizes, with different tensions of elastic members, for different body types/sizes and lifting tasks.

In a fifth embodiment of the invention, an electric motor may be incorporated into the device (e.g., incorporated into the waist belt) and connected to two or more anchors using an elastic member or a non-elastic member such as a cable. The electric motor senses a subject's motions and controls tension in the elastic member or cable on the basis of the subject's body dimensions, load weights, trunk angles and speeds, trunk twists, etc., and controls the length of the elastic member or cable to balance the exerting force.

In a sixth embodiment of the invention, tension of an elastic member can be controlled by the subject. For example, an adjustable knob may be attached to an anchor and an elastic member, such that tension in the elastic member is changed when the knob is turned.

Figure 3:
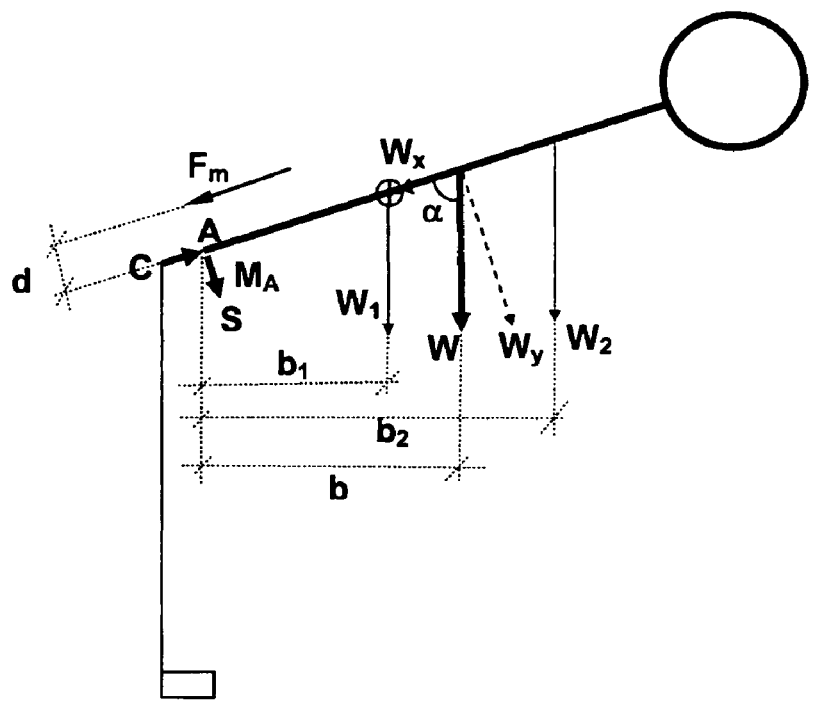
FIG. 3 is a sagittal-plane diagram of erector spinae compressive and shear forces acting on the lumbar spine when a subject lifts an object from the floor (without PLAD)
Figure 4:
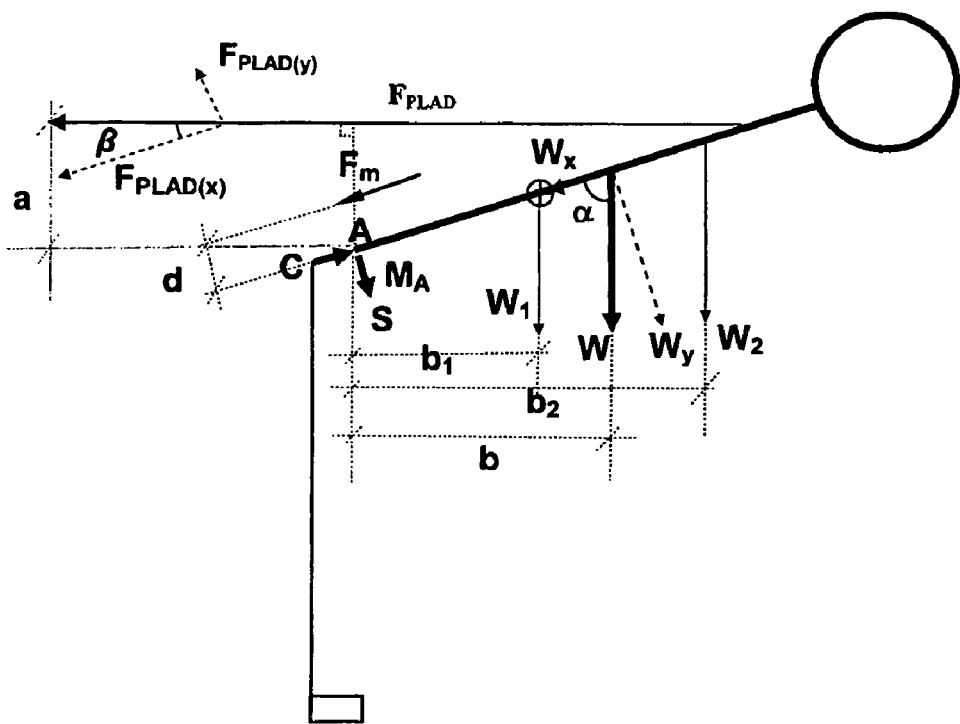
FIG. 4 is a sagittal-plane diagram of erector spinae forces and PLAD forces acting in the lumbar spine when a subject wearing PLAD lifts an object from floor level.

To demonstrate the effectiveness of the PLAD embodiment of the invention, calculations were made to study the activity of a subject's erector spinae muscle during a floor to waist-height lift of an object while wearing the personal lift assist device. Static balance equations were developed (see Example 1) that act about a point "A" in the spinal column. Typically "A" is in the region of the L4/L5 disc or the L5/S1 disc. A summary of the forces generated during such a lift are presented in FIG. 3 (where "$W_1$" is the weight of the subject's upper body, "$W_2$" is the weight of the item being lifted, "W" is the total weight to be lifted by the back muscles which is the sum of $W_1$ and $W_2$, "$W_x$" is the horizontal component of W, "$W_y$" is the vertical component of W, "F," is the force exerted by the erector spinae muscle to effect a lift of W, "d" is the distance between the center of the erector spinae and the center of the L4/L5 intervertebral disc, "A" is a point at the L4/L5 vertebrae joint, "US" is the shear force acting at A during the lift of W, "C" is the compressive force acting at A during the lift of W, "$M_A$" is the sum of the moments at A, "$b_1$," is the horizontal distance between A and the center of mass of $W_1$, "$b_2$" is the horizontal distance between A and the center of mass of $W_2$, "b" is the horizontal distance between the center of mass of W and A, and "a" is the angle of the spine relative to vertical). FIG. 4 depicts the forces when a subject is wearing the PLAD device (where "$W_1$" is the weight of the subject's upper body, "$W_2$" is the weight of the item being lifted, "W" is the sum of $W_1$ and $W_2$, "$W_x$" is the horizontal component of W, "$W_y$" is the vertical component of W, "$F_m$" is the force exerted by the erector spinae muscle, "$F_{PLAD}$" is the force exerted by PLAD, "$F_{PLAD(x)}$" is the force exerted by PLAD in the x-direction, "$F_{PLAD(y)}$" is the force exerted by PLAD in the y-direction, "d" is the distance between the erector spinae and the vertebrae, "A" is a point at the L4/L5 vertebrae, "C" is the resultant compressive force acting at A during the lift of W and is derived in Example 3, "S" is the resultant shear force acting at A during the lift of W and is derived in Example 4, "$M_A$" is the sum of the moments at A, "$b_1$" is the horizontal distance between A and the center of mass of $W_1$, "$b_2$" is the horizontal distance between A and the center of mass of $W_2$, "b" is the horizontal distance between the center of mass of W and A, "α" is the angle of the spine relative to vertical, "β" is the angle of $F_{PLAD}$ relative to horizontal, and "a" is the shortest distance between the spine and $F_{PLAD}$).

All scientific and patent publications cited herein are hereby incorporated in their entirety by reference.

The following examples further illustrate the present invention and are not intended to be limiting in any respect.

EXAMPLES

The human biomechanical system is very complex. Although we can measure many basic properties, other properties cannot be measured. For example, internal forces on spinal structures, redundancy of muscular forces, and coordination of these forces to produce desired motor activities cannot be measured. For this reason, evaluation of the effects of PLAD have been determined by mathematical calculations and by modelling; the results of both methods can be seen in the figures. Mathematical proof that the PLAD can reduce lumbar moments and compressive and shear forces of the hip and knee was first calculated using a simple 2D link segment modelling approach and the equations presented in Examples 1A to 1D. These results were validated by a preliminary electromyography (EMG) study of the erector spinae of one subject performing a lift with and without PLAD. Subsequently, in depth research into the effects of PLAD was performed with many subjects and the effect of PLAD was thoroughly studied by EMG, elastic member strain quantification, and a sophisticated 3-D link segment model.

Example 1

Development of Static Equations for Lifts

A simple two-dimensional model was developed to predict how the erector spinae muscle activity is affected by the personal lift assist device of the preferred embodiment of the invention (shown in FIG. 1). This model can be explained arithmetically through a moment arm analysis of the forces generated during lifting without PLAD (as shown in FIG. 3) and with PLAD (as shown in FIG. 4). The development of static balance equations improves our understanding of forces that act about a point A in the spinal column, typically at the L4/L5 disc or the L5/S1 disc of the spinal column.

Example 1A

Development of Static Equations for Lifts Without PLAD

If we assume the weight of a subject's upper body is "$W_1$," and the weight of the object to be lifted is "$W_2$", then the vertical force exerted to lift a load, "W", can be found using equation 1.

$$W=W_1+W_2 \qquad (1)$$

The distance, "b", between the center of gravity of "W" and the L4/L5 disc of the spinal column is found by equation 2, wherein "$b_1$" is the distance between the center of gravity of the subject's upper body and the L4/L5 disc, and "$b_2$" is the distance between the center of gravity of the object to be lifted and the L4/L5 disc (see FIG. 3).

$$b=(b_1 W_1+b_2 W_2)/W \qquad (2)$$

The distance between the erector spinae and the lumbar vertebrae, or the "effective lever arm", is denoted as "d". An equilibrium equation can be obtained for the sum of the moments at a point A, denoted "$M_A$" where the force exerted by the erector spinae muscle is denoted as "$F_m$".

$$\Sigma M_A=0=F_m d-Wb \qquad (3)$$

The force exerted on the erector spinae muscle, "$F_m$", can be calculated with equation 4:

$$F_m=Wb/d \qquad (4)$$

The compressive force, "C", acting on the lumbar spine is then given by equations 5 to 7 where α is the inclination of the trunk to vertical.

$$C=F_m+W\cos\alpha \qquad (5)$$

$$C=Wb/d+W\cos\alpha \qquad (6)$$

$$C=W(b/d+\cos\alpha) \qquad (7)$$

The amount of the compressive force acting on the lumbar spine is a minimum value which neglects stabilizing activity created by the co-contraction from other trunk muscles.

The shear force, "S", acting on the lumbar spine is then given by equation 8:

$$S=W\sin\alpha \qquad (8)$$

Example 1B

Development of Static Equations for Lifts with PLAD

We may quantify the affects of wearing the PLAD embodiment of the invention pictured in FIG. 1 by adding it to the relevant equations. FIG. 4 depicts the parameters involved with a subject wearing such a device. The force exerted by the erector spinae muscle, "$F_m$", in this condition can be calculated with equation 10 where the force exerted by the device is represented as "$F_{PLAD}$" and the distance between the anchor of the lower back and the L4/L5 disc, or moment arm of the device, is denoted as "a".

$$F_m d+F_{PLAD}a-Wb=\Sigma M_A=0 \qquad (9)$$

$$F_m=(Wb-F_{PLAD}a)/d \qquad (10)$$

Comparing equations 4 and 10 shows that the amount of force exerted by the erector spinae when a subject is wearing PLAD and bending from the waist to lift an object from the floor, is an amount [$F_{PLAD}a/d$] less than the same situation without PLAD, where the distance between the erector spinae and lumbar vertebrae, "d", is constant.

The compressive force acting on the lumbar spine, "C", is given by equation 12 where "β" is the angle between "$F_{PLAD}$" and horizontal.

$$C=F_m+W\cos\alpha+F_{PLAD}\cos\beta \qquad (11)$$

$$C=(Wb-F_{PLAD}a)/d+W\cos\alpha+F_{PLAD}\cos\beta \qquad (12)$$

The angle between "$F_{PLAD}$" and the back muscles is negligible, so cos β is close to zero. Therefore, the amount of compressive force for a subject wearing PLAD is decreased by an amount [$F_{PLAD}(1-(a/d)]$ where "d" is constant. The compressive force can be decreased further by increasing the distance "a" (see reference numeral 20 in FIGS. 1 and 2). A distance of 20 cm for "a" has been used in the prototypes of PLAD tested to date. The shear force "S" acting on the lumbar spine when a subject wears PLAD can be calculated with equation 13:

$$S=W\sin\alpha F_{PLAD}\sin\beta \qquad (13)$$

By comparing equations 8 and 13, it is apparent that by wearing PLAD it is possible to oppose the shearing force of the upper body and decrease it by an amount [$F_{PLAD}\sin\beta$]. As a point of reference, many lifting tasks incur compressive forces of around 4000 N and shear forces of around 500 N (Shirazi-Adl et al., 1986).

Example 2

Preliminary Study to Determine the Effect of PLAD on the Compressive and Shear Forces Experienced by a Subject To obtain a preliminary quantification of the effect of wearing PLAD on the compressive and shear forces exerted on the body, a study was conducted with one human male subject. This subject lifted a 10 kilogram object from floor to waist height using a stooped posture with and without wearing the first prototype of PLAD (see FIG. 5 where "$F_{PLAD}$" is the force exerted by the PLAD device, "$F_m$" is the force exerted by the erector spinae muscle, "$W_1$" is the weight of the subject's upper body, "$W_2$" is the weight of the item being lifted, "W" is the total weight to be lifted which is the sum of $W_1$ and $W_2$, "S" is the shear force acting at a point on the spine during the lift of W, and "C" is the compressive force acting at a point on the spine during the lift of W). The subject was videotaped at 30 Hz with a Panasonic™ digital camera at right angles to the lifting task. The variables (a, b, α, P and length of the elastic members) were digitized using custom software (DIG™, developed in the Biomechanics Laboratory, Queen's University at Kingston, Kingston, Ontario, Canada). These variables were used to measure joint coordinates, body angles, relevant anthropometric dimensions, and distances between the load and related locations in different angles during lifting. The data extracted from the software program, and the equations of Examples 1A and 1B were used to quantify the effect of PLAD on the erector spinae.

This study together with a study of the tension developed within the elastic elements of the PLAD (see Example 3 and FIG. 9) allowed preliminary quantification of the effect of PLAD on compressive and shear forces acting on the subject's back. It was determined that PLAD reduced compressive force at the L4/L5 intervertebral joint by approximately 600 N and reduced shear force at the L4/L5 intervertebral joint by approximately 140 N. With this result, the study outlined in Example 9 was undertaken to obtain statistically significant quantification of the effect of PLAD on reducing compressive and shearforces acting on the back.

Example 3

Effect of Material and Configuration Changes to Elastic Members, and Determination of $F_{PLAD}$ Values The amount of energy that may be stored and released from a deformed elastic member is determined by its configuration and/or the material of which the elastic member is made. Examples of different configurations of elastic members for the shoulder to waist portion of PLAD are crossed, straight, side or a combination thereof. In a study of the resultant forces ($F_{PLAD}$) exerted by the device, known weights were systematically added to elastic members made of various materials to study the elastic member stress-strain relationship. Regression equations were used to derive the stretch coefficients, "k", for the elastic members in different configurations. These stretch coefficients were determined from the slope of the graphs of FIG. 9 which graphically displays equation 14, where "j" is the distance of deformation (i.e., displacement) of the elastic member.

$$F_{PLAD} = kj \quad (14)$$

As expected, it was determined that "$F_{PLAD}$" increased as the amount of deformation (e.g., stretching) of the elastic member increased. The particular elastic member used for the study described in Example 2 was selected based on the typical amount of deformation seen during lifting tasks (see FIG. 9(*a*) and 9(*b*)). It was observed that when a subject used a squatting lifting technique, there was minimal deformation (i.e., stretching) of the elastic member of approximately 10 cm and the $F_{PLAD}$ was approximately 75 N to 100 N. When a stooping lifting technique was used, there was approximately 25 cm of deformation and $F_{PLAD}$ was approximately 150 N to 175 N.

Example 4

Calculated Effect of PLAD on Erector Spinae Based on Mathematical Calculations By inserting $F_{PLAD}$ values obtained from the study described in Example 2 into equation 12, $F_m$ values were determined for many angles of the upper body to vertical. By using equation 5 and data gathered for the study described in Example 2 for a subject moving from a stooped to a standing posture, resultant (FIG. 6), compressive (FIG. 7), and shear (FIG. 8) forces were calculated for a point A located near the L4/L5 disc of the spine. It was determined that when the subject is wearing PLAD, the amount of force exerted by the erector spinae is less than without PLAD. The effect of PLAD is greatest at large angles, e.g., angles greater than about 30° from vertical.

Figure 7:
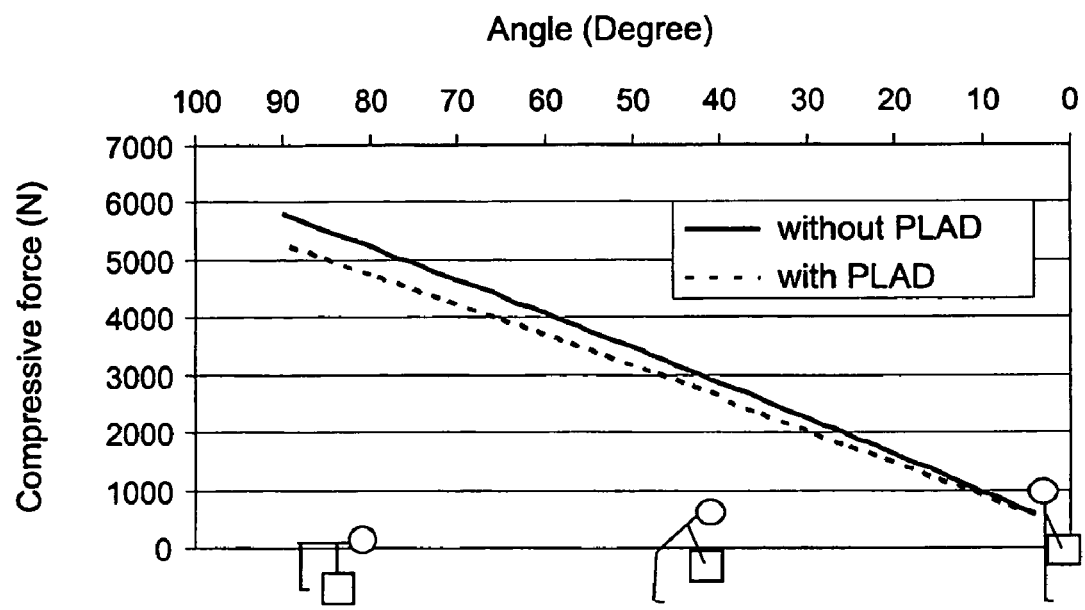
FIG. 7 is a graph showing the calculated compressive force exerted on the L4/L5 disc of a subject lifting a 10 kg object with and without PLAD.

FIG. 7 compares the compressive force exerted on the L4/L5 disc at different angles with and without PLAD. A larger moment arm of the device, or distance between the L4/L5 disc and the waist-level anchor point "a" of force application of the device (see 20 in FIG. 1), leads to smaller compressive force requirements by the erector spinae muscles. However, one must balance this with practical issues such as bulkiness of the device. A moment arm of 20 cm was used in this study.

Figure 8:
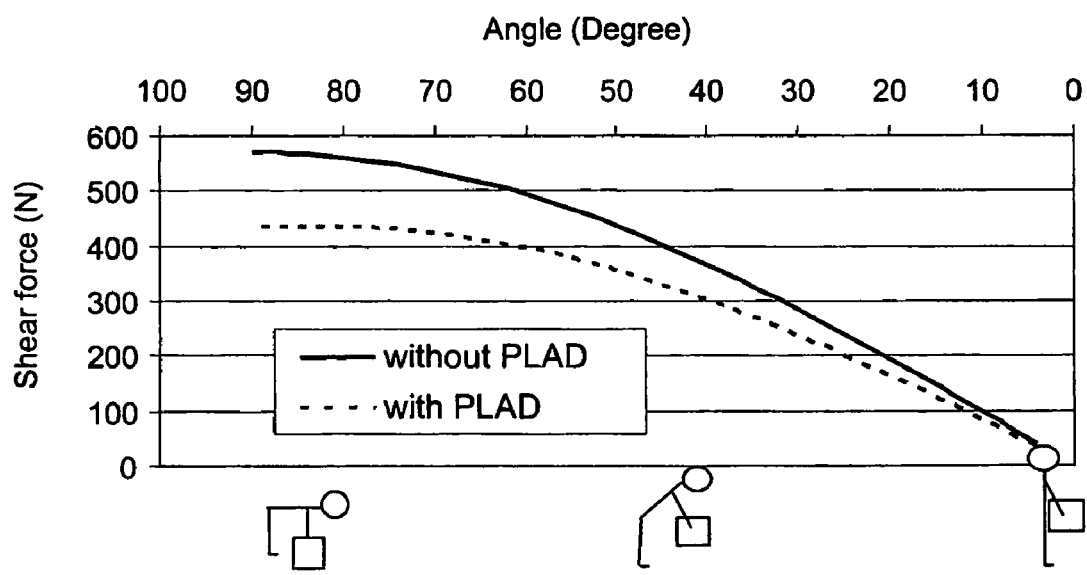
FIG. 8 is a graph showing the calculated shear force exerted on the L4/L5 disc of a subject lifting a 10 kg object with and without PLAD.

The amount of shear force exerted on the L4/L5 disc was calculated from equations 8 and 13. FIG. 8 depicts the results with and without PLAD. PLAD is able to oppose the shear force exerted from the upper body and the lifted object. It is important for safety to minimize the magnitude of shear force on the spine (McGill, 1997).

Example 5

Calculated Effect of PLAD on Erector Spinae Based on Modelling

Using the physical constraints of body motion and by estimating the forces acting on different component structures, we can reasonably predict the magnitudes of spinal forces for loads held in various postures. For a better understanding of PLAD's effects on the erector spinae, a first generation model was created in AutoCAD™ 2002 (Autodesk, Inc., San Rafael, Calif.) and the ACIS format was transferred to Visual Nastran 4D® 2003 (MSC Software Corp., Santa Ana, Calif.). The elastic members used in PLAD were assumed to be similar to a linear spring constraint in this program. A shaft was attached to the upper body in a manner similar to that of a spine. A revolute motor was applied at the end of the shaft to lift the upper body modelling the erector spinae.

To find the forces exerted on the erector spinae on the basis of this model, the calculated torque around the revolute motor ($M_A$ in FIG. 4) was found. As seen in equation 15, dividing the torque or moment around the z-axis, by the distance between the spine and erector spinae, "d", gives the amount of force ($F_m$) exerted by this muscle.

$$F_m = M_z/d \qquad (15)$$

The distance between the erector spinae and the spine, "d", (the moment arm distance), was considered to be 6 cm for an average person. The resultant force exerted by the erector spinae as found by modelling is shown in FIG. 10; for comparison, the calculated resultant force is shown in FIG. 6. These figures show that there is a significant difference between the forces exerted by the erector spinae when PLAD is worn and when it is not, with less force when PLAD is worn.

There are some differences between the calculated results and the results found by modelling, for example, in terms of curve shape and magnitude. The model lifts the load dynamically (20 degrees/sec), therefore it calculates the effect of the upper body and load acceleration on the produced model. Thus it shows higher values at the beginning and smaller values at the end of the lift, perhaps because the lever arm gets shorter.

Figure 11:
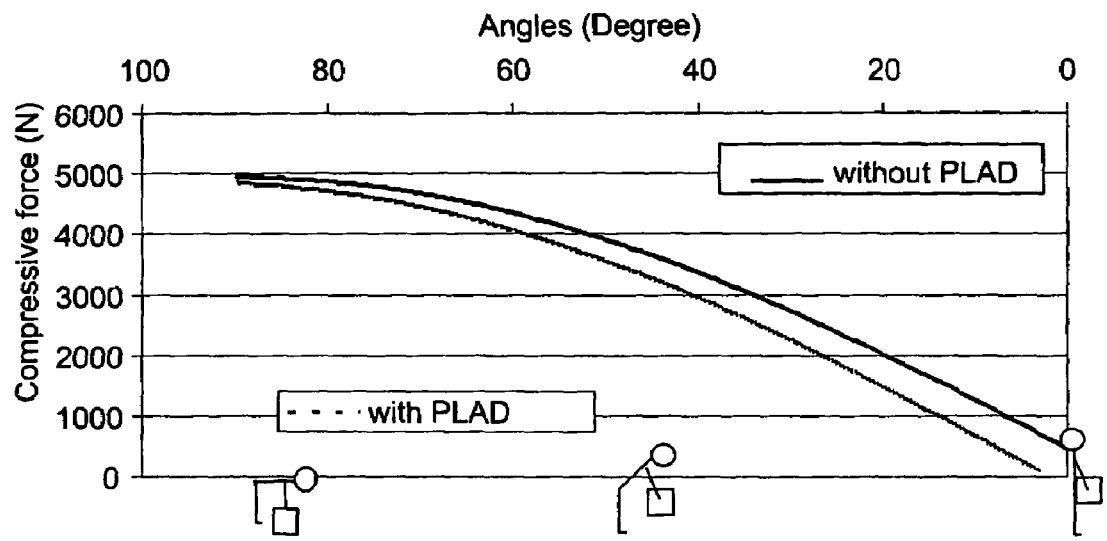
FIG. 11 is a graph showing modeled compressive force exerted on the L4/L5 disc of a subject lifting a 10 kg object with and without PLAD.
Figure 12:
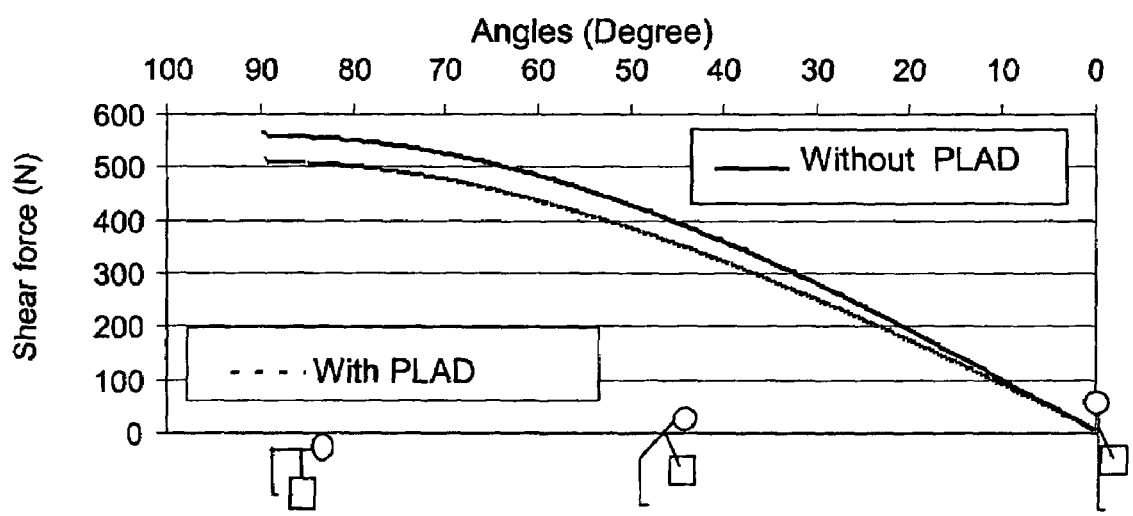
FIG. 12 is a graph showing modeled shear force exerted on the L4/L5 disc of a subject lifting a 10 kg object with and without PLAD.

Compressive and shear forces exerted on the L4/L5 disc were found by modelling the forces along the shaft of the model and the erector spinae, with results show in FIGS. 11 and 12. These modeled results can be compared to calculated results shown in FIGS. 7 and 8. Results of the modelling and the calculations agree in that decreased compressive and shear forces are experienced by the PLAD user. The higher compressive force at the beginning of a lift is likely due to greater acceleration of the upper body and a higher lever arm compared to the end of the lift.

Example 6

Calculated Effect of PLAD on Hip and Knee Forces Based on Mathematical Calculations PLAD transfers compression force from the upper body to the lower body. It relies on the subject's hip to act as a fulcrum and transfers the weight of the upper torso to the lower leg at the level of the leg's tibial tuberosity and/or feet (see FIGS. 1 and 2). The tibial tuberosity or tibial plateau below the knee is a strong bony area which is the site of attachment of the quadriceps muscles, and it also bears the body weight of people with prosthetic devices for below-knee amputations.

Figure 13:
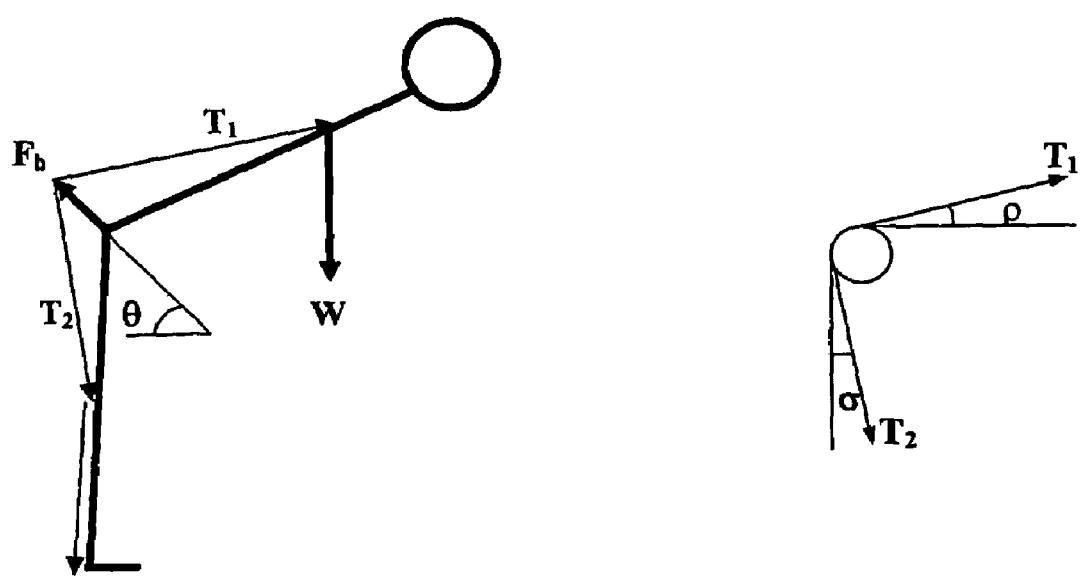
FIG. 13 is a diagram showing a biomechanical analysis of the forces on the hip area of a subject during a lift.

This example determines how much force is exerted on the hip and how much is exerted on the tibia in a subject wearing the preferred embodiment (FIG. 1). FIG. 13 shows the force vector analysis in the hip area where p is the angle between the tension force vector of the upper-body elastic members ($T_1$) relative to horizontal, $\sigma$ is the angle between the tension force in the lower elastic member ($T_2$) relative to vertical. The $\rho$ and $\sigma$ angles (FIG. 13) were found by the DIG™ digitization software developed at Biomechanics Laboratory, Queen's University at Kingston, Ontario. The reaction force vector on the hip ($F_h$) is angled relative to horizontal, this angle is represented as $\theta$. The equilibrium equations for the force exerted by PLAD on the hip are equations 16 and 17, where the force along the x-axis is denoted "$F_x$", and the force along the y-axis is denoted "$F_y$".

$$\Sigma F_x = 0 = -F_h \cos\theta + T_2 \sin\sigma + T_1 \cos\rho \qquad (16)$$

$$\Sigma F_y = 0 = F_h \sin\theta + T_1 \sin\rho - T_2 \cos\sigma \qquad (17)$$

$T_1$ (and similarly $T_2$) was determined from equation 14 where the coefficient "k" is determined as discussed in Example 6, and where "j" is the distance of the deformation of the elastic member. $T_1$ and $T_2$ were also measured directly and the results agreed with those obtained from equation 14.

Figure 14A:
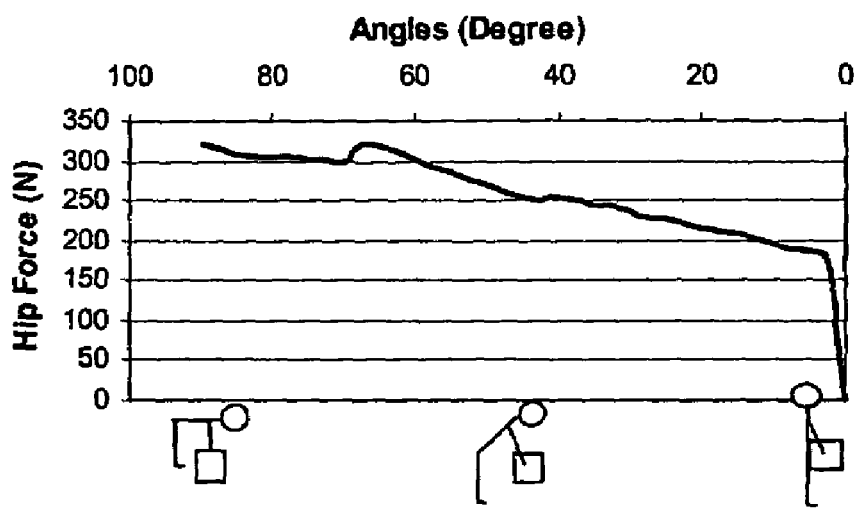
FIGS. 14(a) and (b) are graphs showing modeled force exerted by PLAD on the (a) hip and (b) tibia of a subject lifting a 10 kg object (the tibia values are the sum of forces exerted on both tibial tuberosities)
Figure 14B:
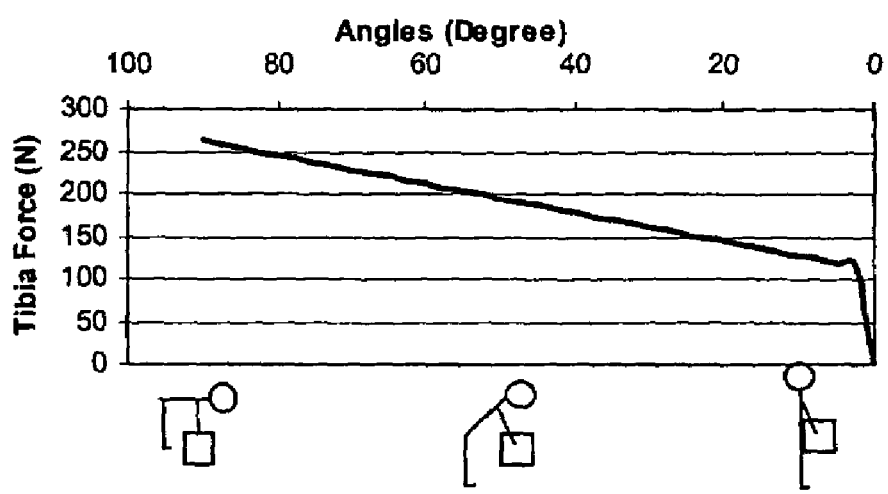

Typical point force magnitudes experienced at the hip by a subject wearing PLAD range from 125 N to 325 N, as shown in FIG. 14. The hip level force of PLAD acts on the pelvic girdle, and not the lumbar vertebrae. The pelvic girdle is a solid bony structure that is well adapted to receiving force. These forces, when spread evenly across the back of the pelvis, are well within the compressive strength characteristics of bone (Hobson 1992).

Example 7

Calculated Effect of PLAD on Hip and Knee Forces Based on Modelling

Figure 15:
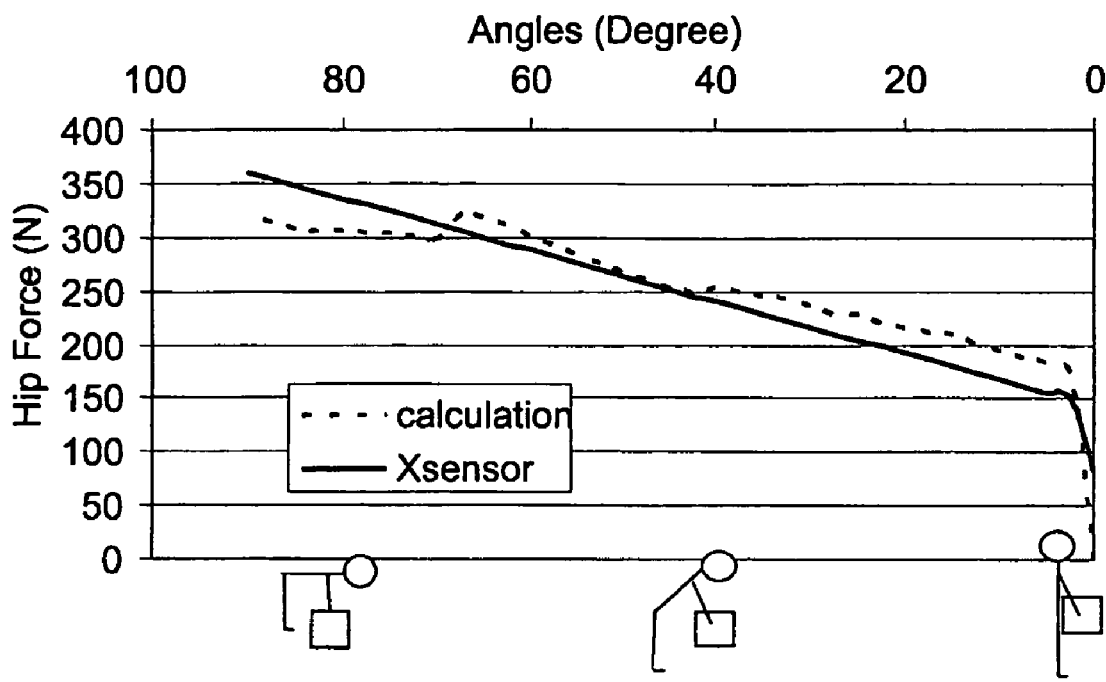
FIG. 15 is a graph showing calculated and Xsensor™ measured force exerted on the hip by the PLAD device when lifting a 10 kg object.

To validate the above described mathematical constructs, a validation study was performed using one subject. In this study, measurements of the external reaction forces applied by the PLAD to the subject at the site of the waist belt (at the hips on the pelvic girdle) during a lift were made. The measurements were acquired using an Xsensor™ Pressure Mapping System (Xsensor™ Technologies Corp., Calgary, Alberta), comprised of a blanket matrix of capacitance pressure sensors (420 mm×420 mm). The Xsensor™ blanket was placed between the lower back of the subject wearing PLAD, and the PLAD waist belt. To calibrate the Xsensor™ system, a known force was then applied to the Xsensor™ blanket while the subject wearing PLAD and the Xsensor™ blanket lay on his/her stomach. The subject wearing the PLAD and the Xsensor™ blanket then stood upright and lifted a 10 kg object from the floor to waist height and data were collected over the course of the lift. Data from each sensor were received by a computer, converted to force using Force=Pressure×Area, and used for analyses. The calculated forces at the hip area are shown in FIG. 14 and the calculated and measured results on the waist belt (hip area) are shown in FIG. 15. There is a linear relationship between the angle of the subject's torso and the forces exerted on the hip and tibial tuberosis. As the subject leaned forward, the force exerted on the hip increased. The similarity between this approach and that of Example 6 confirmed that the mathematical approach makes a reasonable approximation of the actual forces on the pelvis.

Example 8

Effect of PLAD on Erector Spinae Based on Electromyography (EMG) of Erector Spinae Muscles of One Subject A study using electromyography (EMG) of the erector spinae muscles was conducted to determine PLAD's effectiveness in reducing demands on the erector spinae muscles. Reduced demand should be reflected by less EMG activity in the erector spinae muscles during a PLAD supported lift. As shown in Example 1B, by wearing a PLAD device a subject experiences reduced compressive and shear forces. To confirm this finding, one healthy 25 year old male subject was tested. The skin overlying the subject's erector spinae at the levels of T10 and L3 vertebrae was cleaned with alcohol and abraded with skin preparation pads. Two pairs of disposable ECL 135 Medi-Trace™ Mini electrodes (Graphics Control Corp., Buffalo, N.Y.) were attached over the erector spinae muscles about 4 cm from the midline of the back. A fifth electrode was positioned over the spinous process of the T1 vertebrae as a reference. A Bognoli 16 Channel Electromyography System (Delsys Inc., Boston, Mass.) was used to collect the EMG signal. The EMG signal was filtered with a band-pass filter of 5-300 Hz, A-D converted at 500 Hz, full-wave rectified, averaged with a time interval of 0.02 s, and recorded on a microcomputer.

The subject stood in front of a waist-height table with an 10 kg object on the floor. He lifted the object from floor to table in 2×10 trials, the first ten trials with PLAD and the second ten trials without PLAD. The PLAD device used in this study had four elastic members in parallel configuration, the two on the back were Thera-Band™ tubes and the two on the legs were bungee cords, the subject's particular style of lifting was a stooped posture and required about 2 seconds to complete the entire lift cycle. A program written in Labview™ announced the time to start the forward bend by an audible tone. After 2 seconds, another audible tone was emitted by the computer to signal the end of the lift. An accelerometer attached to the load allowed tracking of the start and end of the lifting cycle in the collected EMG data.

Figure 16:
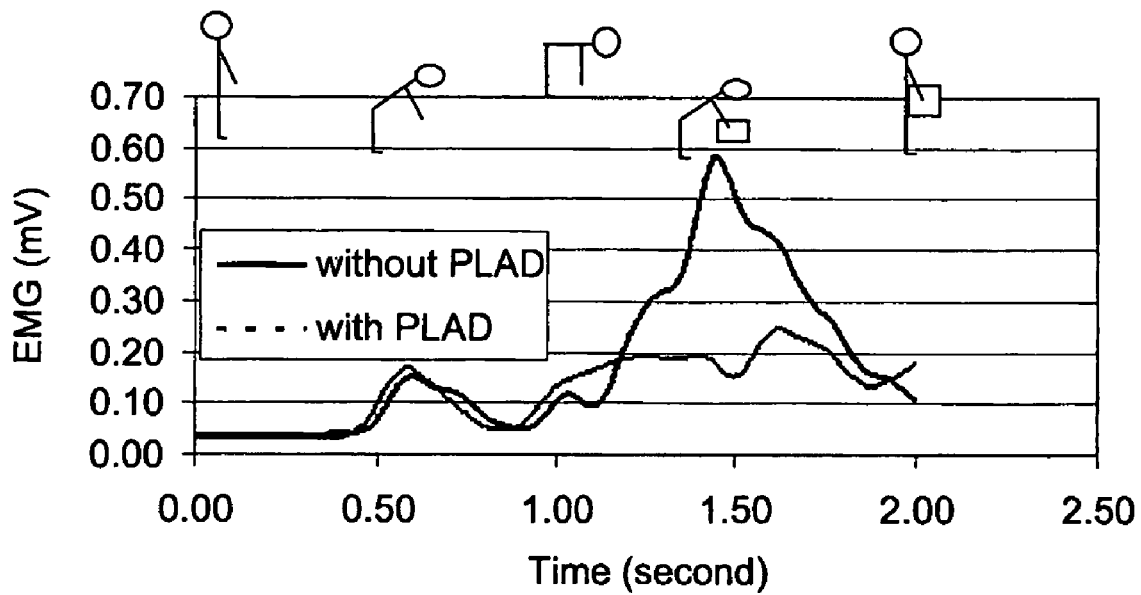
FIG. 16 is a graph showing electromyography of the erector spinae of one male subject lifting a 10 kg box with handles, with and without PLAD, using a stoop position and starting 25 cm from the floor (handle height) and ending at waist height.

The results are presented in FIG. 16. These profiles represent the time from initial standing to stooping to collect the box and then standing up to place the box on the desktop. Although only one subject was used, all trials reflected a reduction of EMG activity during the upward lifting phase when PLAD was used. Lumbar flexion increased smoothly as the subject bent forward until a peak in the EMG signal indicated that the action of the back muscles was decelerating the upper body. While the object to be lifted was being grasped, a dip in the EMG trace suggested a momentary 'flexion-relaxation' phenomenon. The EMG signal then reached its main peak as the weight was lifted. This second and larger peak in the EMG signal was influenced by the rapid shortening of the muscles as the lumbar spine was extended (Dolan and Adams, 1993). It was clearly established by this trial that PLAD is effective in reducing demands on the erector spinae muscles as measured by reduced EMG activity in the erector spinae muscles during a PLAD supported lift.

Example 9

Effect of PLAD Through Testing of Human Subjects

Using data acquired through human subject box lifting trials, two objective assessment methods are presented below that show PLAD's effectiveness in reducing the forces and moments on the lumbar spine. The first method (Example 9B) uses electromyography measurements to demonstrate that there is a reduction in the activity of the erector spinae muscles, thus indicating a reduction in back muscle force requirements for a lifting task when PLAD is used. The second approach (Example 9C) demonstrates mathematically that some of the force requirements during lifting are redistributed from the back muscles to the PLAD, thus reducing the back muscle force requirements.

Example 9A

Procedural Details for Box Lifting Trials

After the ethics process (approved by Queen's University at Kingston), subjects were asked to follow a standardized data collection procedure that was designed to randomize trials and minimize fatigue for all human experiments. Ten males and ten females between 18 to 30 years of age with no history of back pain or other musculoskeletal problems or cardiovascular problems were recruited for each PLAD/no PLAD experiment. Following the experiments, all twenty subjects reported that PLAD provided assistance when performing the lifts. At the time of writing, data for the females had not been analyzed. Accordingly, data for the male subjects will be discussed herein. The EMG data for one of the ten males was not recorded; the data presented for the box lifting trials is for nine male subjects.

Anthropometric data for each subject was used to determine body locations for 12 Fastrak®motion sensors (Fastrak® Electromagnetic Tracking System, Polhemus Inc., Colchester, Vt.). To capture the 3-D position data of the body during box lifting trials, these motion sensors were attached to a subject's skin over the appropriate landmarks on arms (hands, forearms, upper arms), thighs and the head, as well as at the trunk center of mass and L4/L5 spinous processes as known in the art. Then, eight bipolar EMG electrodes (Delsys Inc., Boston, Mass.) were fixed bilaterally over the following muscles of the trunk according to sites recommended by McGill et al. (1986) and Cholewicki et al. (1996): erector spinae (5 cm from the spinous process) at the level of the fourth lumbar vertebrae (L4); erector spinae (5 cm from the spinous process) at the level of the ninth thoracic vertebrae (T9); external oblique at the level of the belly button (and 10 cm laterally); and rectus abdominus at the level of the belly button (and 3 cm laterally). Before the lifts were performed, the EMG signals were normalized with respect to maximal isometric contractions using standardized postures designed to maximally activate the erector spinae, rectus abdominus and external oblique muscle groups.

The PLAD device used for this study was similar to that described above (see FIG. 1). Four elastic members were used to connect the shoulder belt anchors to the waist belt anchor. A first pair of these elastic members was connected in a substantially parallel arrangement, as in FIG. 1, while the second pair of elastic members was connected in a crossed arrangement, as in an "X" formation. The PLAD was easily adjustable to allow for different body sizes. Different colours (colours indicate strength or resistance to stretch) of Thera-Band™ elastics were used initially. However, grey coloured Thera-Band™ were preferred by most subjects and subsequently, the box lifting trails were performed with grey coloured Thera-Band™ used for the elastic members of the upper body portion of PLAD.

Bungee cords were used as for the elastic members of the lower body portion of PLAD. The waist belt lever arm "a" (reference numeral 20 in FIG. 1) was 20 cm in length. All six of the elastic members had strain gauges attached in series between the elastic members and the waist belt anchor. The strain gauges were custom made (Department of Mechanical Engineering, Queen's University at Kingston, Kingston, Ontario) from a flat dog-bone shaped piece of solid aluminum with a hole in either end and a micromeasurement strain gauge (part number EA13-125TG, Measurement Group Inc., Raleigh, N.C.) adhered to its central portion. Loops of wire threaded through the holes in the strain gauges attached the strain gauges to the waist anchors and the elastic members. The signals from the strain gauges were amplified by an A-Tech Strain gauge amplifier 600 (A-Tech Instruments Ltd., Scarborough, Ontario). A synchronization switch on each box was used to synchronize the EMG and 3-D position data for the start and end of each lift.

Figure 2:
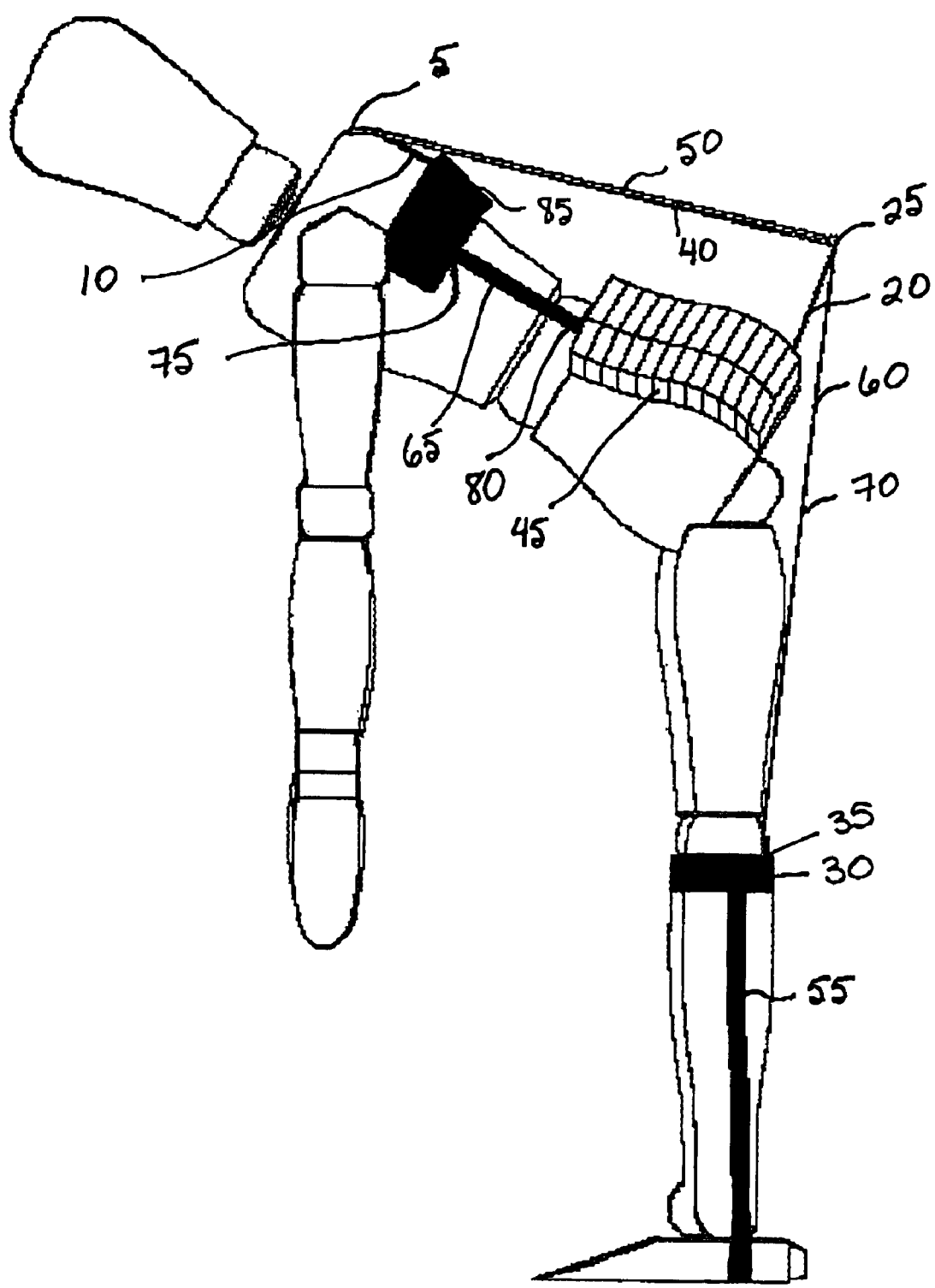
FIG. 2 is a drawing of an embodiment of the invention wherein anchors are placed at the shoulders, below the knees, at the lower back, at the upper back on the subject's side, at the lower back on the subject's side, and elastic members connecting the anchors and looped around the foot.

Each subject then followed a standardized data collection procedure of performing box lifts. Each box had two handles located on either side and 25 cm from the bottom of the box, so all lifts began at 25 cm from the floor although the wording "from floor to waist height" may be used. Male subjects lifted 5 kg, 15 kg and 25 kg boxes, and female subjects lifted 5 kg, 10 kg and 15 kg boxes using freestyle, stooped or squat lifting styles in either asymmetric or symmetric conditions. A total of 54 lifts were performed by each subject under PLAD/no PLAD conditions. Once all of the lifting conditions (three weights, three techniques and three postures) were completed successfully for the PLAD (or no PLAD) condition, the subject was fitted for the no PLAD (or PLAD) condition, the trial order was randomized, and the lifts were repeated. During the box lifting trails, data were collected simultaneously from the twelve Fastrak® sensors, six elastic member strain gauge sensors, eight EMG electrodes and the synchronization switch on two synchronized computers, displayed, and stored in separate files. At the end of the testing session, subjects were given a comfort questionnaire and a pressure points/range of motion questionnaire. The results of the questionnaire were that all twenty subjects felt that PLAD had assisted them to perform all of the lifts, and subjects with sufficient upper body weight to cause 200 N of force to transfer to the lower leg (at the tibial tuberosity) commented on minor discomfort. An embodiment with a loop around the foot (as shown in FIG. 2) may be preferred in such cases.

Example 9B

EMG Study

Processing of EMG data involved removal of baseline noise, signal rectification, expression of EMG as a percentage of maximal isometric contraction and smoothing with a 2.7 Hz double-pass Butterworth filter. Data were reduced to the start of downward trunk motion, through the lift and end of trunk extension. Data were then normalized to a 100% time base. Then at each time interval, data were averaged and standard deviations calculated to provide ensemble averages for each muscle for each trial condition.

Since the amount of muscle electrical activity detected with EMG can be roughly equated to muscular force output, it is possible to ascertain the demand on muscles with PLAD and without PLAD. If the amount of electrical activity is reduced, then the muscle force requirements are also reduced. Since the load being lifted is a constant between conditions, PLAD is responsible for this reduced muscular force requirement.

Figure 17:
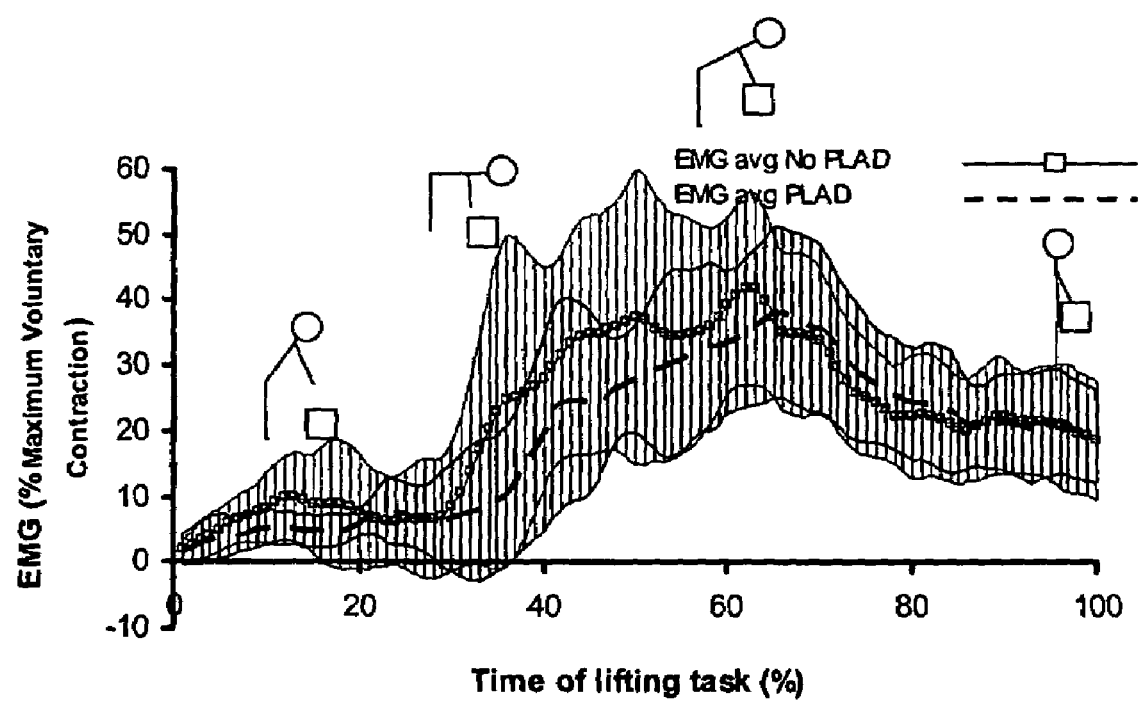
FIG. 17 is a graph showing the average and standard deviation electromyography of the erector spinae for nine male subjects who lifted a 15 kg box with handles, with and without PLAD, using a stoop position and starting 25 cm from the floor (handle height) and ending at waist height.

Throughout the lifting cycle the PLAD EMG activity was smaller than the no PLAD condition, especially when the PLAD elastic elements were stretched during the lift. This was especially true for the start of the lift where greater forces were needed to get the load off the floor. Overall, the EMG data indicated that PLAD reduced the demand on back musculature by 2% to 25% (FIG. 17). This was confirmed for all lift conditions and EMG locations from the mean ensemble average and the standard deviations. An example of such data for nine male subjects for the stoop lift condition and at the L4 vertebrae EMG location is shown in FIG. 17. From this study, it is thus expected that PLAD can reduce the risk of lower back injury and pain, and accelerate recovery from back injury.

Example 9C

Elastic Member Strain Gauge Study

The forces measured by the six strain gauges mounted on the PLAD in series with the elastic members ranged from approximately 50 N to 200 N and assisted with the initial phase of the lift. In terms of reduction of erector spinae muscle force required for a lift, this result translates into a 400 N to 1300 N reduction in muscle force required by the erector spinae. This result was consistent across all subjects, loads, techniques and postures and confirms that the PLAD reduces the compressive and shear forces at L4/L5 and reduces the amount of erector spinae activity during a variety of lifting conditions.

Example 9D

3-D Dynamic Models for PLAD Analysis

Two dynamic biomechanical models were developed to estimate moments on the lumbar spine in three dimensional tasks with and without PLAD. For visual dynamic analysis of PLAD, a model was developed in Visual Nastran 4D® (VN model), a dynamic mechanical modelling program that can be integrated with other software and aid with the design process. The second model was based on the Hof model which has already been validated by Plamondon et al. (1996).

3-D Linked-Segment Model Created in Visual Nastran 4D®

A 3-D linked-segment model (VN model) was created using Visual Nastran 4D® software. This model can be used to calculate the mechanical torques and forces at any defined joint within the VN model. In this example, the VN model was used to determine L4/L5 moments and compression and shear forces. The data acquired by the twelve Fastrak sensors of the box lifting trials (see Example 9A) were inputs to the VN model, and other programs were written to extract and apply the position and rotation data of the Fastrak sensors. For example, Simulink™ and Matlab™ programs read, controlled, and assigned the data from each body segment to the VN model. The VN model also received and assigned data from six strain gauges attached to the elastic members on the PLAD device (see Example 9C) to calculate the moments during PLAD application. The data entered the VN model through Simulink™ where euler angles, which represent the orientation of each body segment with respect to a ground reference frame, were manipulated using transformation matrices, to calculate the angles between each two adjacent body segments based on the euler angles of the two segments. Three revolute motors in X, Y, and Z directions were mounted on each simulated joint to assign the angles to adjacent body segments and measure the forces and moments based on angular and positional changes (flexion-extension, lateral bending, and rotation, respectively).

Validation of the VN Model

There are several well-established linked-segment biomechanical models in the scientific literature, some of which incorporate EMG data with data from body landmarks and accelerations of body segments. However, the VN model is unique to this application. Hence, it was important to demonstrate its validity in resolving the forces and moments at each joint. The approach used for validation was the Hof (1992) model.

A Labview™ program was written to take the ten Fastrak™ sensor positions and orientations and find the 3-D moments exerted on the L4/L5 position. The program also received data from the strain gauges attached to the elastic members of the PLAD (see Example 9C) and calculated the moments at L4/L5 during PLAD use. To estimate the moment with respect to an arbitrary moving position P, the equations presented by Plamondon et al. (1996) were used.

The net reaction forces at the L4/L5 position were calculated with an upper body model only. The reaction moments are reported about the three orthogonal orthopaedic axes on the trunk at L4/L5. The moments in flexion/extension (X-axis), lateral bending (Y-axis), and axial rotation (twisting) (Z-axis), are about the transverse axis, sagittal axis, and longitudinal axis of the trunk, respectively. Joint forces and joint moments at L4/L5 were calculated with and without PLAD for 20 subjects.

Figure 18:
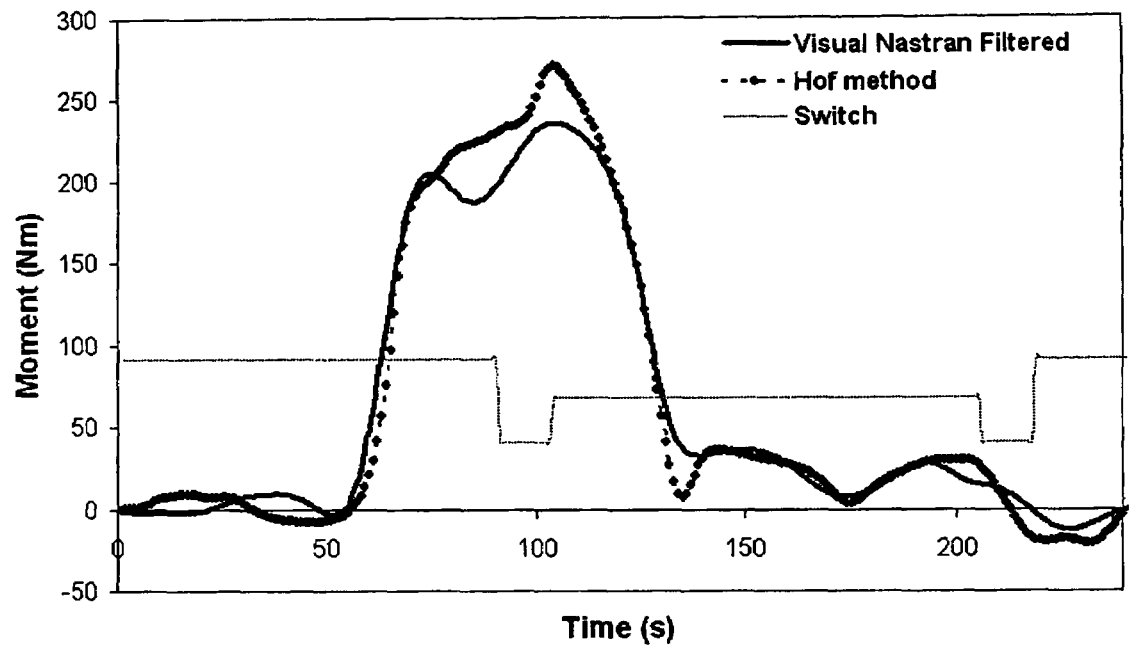
FIG. 18 is a graph showing the net lumbar moment about the L4/L5 joint as calculated using the Hof method and as determined using a model created with the Visual Nastran 4D® modelling program.

FIG. 18 shows a comparison of the VN and Hof models, and validates the VN model. From this figure, the VN model appears to be more conservative than the Hof model, which may be attributed to errors in anthropometrics and in estimation of body segment endpoints. Despite this underestimation, this result confirms that the VN model can be used to assist with PLAD design in a virtual environment.

Figure 19:
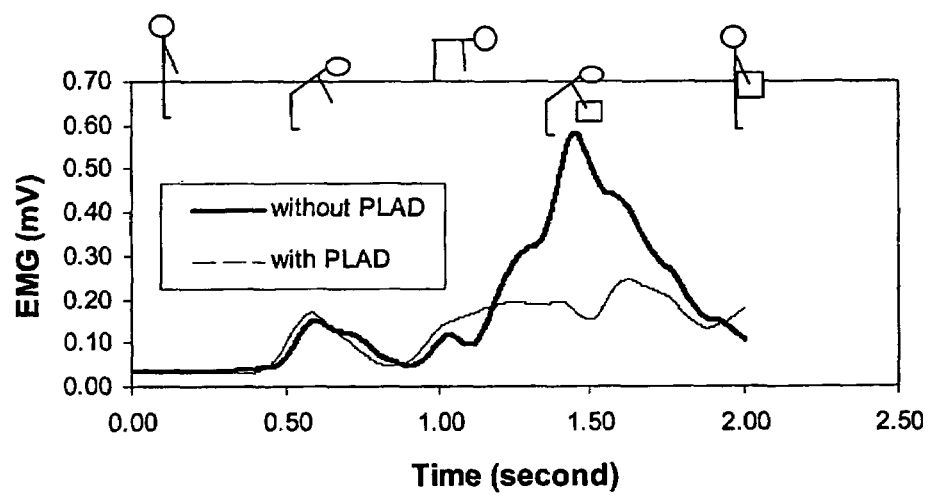
FIG. 19 is a graph showing flexion and extension about the x-axis moment at the L4/L5 joint for one lift with and without PLAD, as determined using a model created in the Visual Nastran 4D®) environment.

Moment results of the VN model for one lift during flexion-extension (X moment) at the L4/L5 position is shown in FIG. 19. The greatest magnitude of the X moment occurs during the final stage of lowering and first stages of lifting. It is at this stage that the elastic members are under their greatest deformation (stretch). There is approximately a 25% reduction in the moment about L4/L5 during this phase. This reduction in force is transferred by PLAD from the back to other places in the body, namely the two attachment points at the shoulders and lower legs. The moments about the Y axis (lateral bending) and Z axis (rotation) were much smaller than the moment about the X-axis (flexion-extension). This pattern was repeated for each lifting task. The elastic member strain-gauge sensors also verified that the PLAD was reducing force by about 300 to 400 N for all lift types.

Example 10

Effect of PLAD on Hip Extension

To this point, the effectiveness of PLAD in reducing forces required by the back muscles has been demonstrated. This example describes the effect of PLAD on hip extension. There is a contribution between the spine and leg muscles during lifting tasks. The leg muscles are responsible for extending the trunk and for holding it during a static task, especially for a long period of time. Our results show that the elastic members parallel to the leg muscles also improve the efficiency of lifting. To model this, a free body diagram of the forces exerted on the hip during flexion of the trunk (bending in stoop or squat posture) was developed.

To find the moment about the hip joint with and without the PLAD in two dimensions, two translational forces and one rotational moment are required. When the PLAD is added, other forces, including the tension force of the elastic member exerted on the upper body and the tension force of the elastic member exerted on the legs, produce a resultant force applied to the hip. The required equations have been developed and simulations are in progress.

Figure 20:
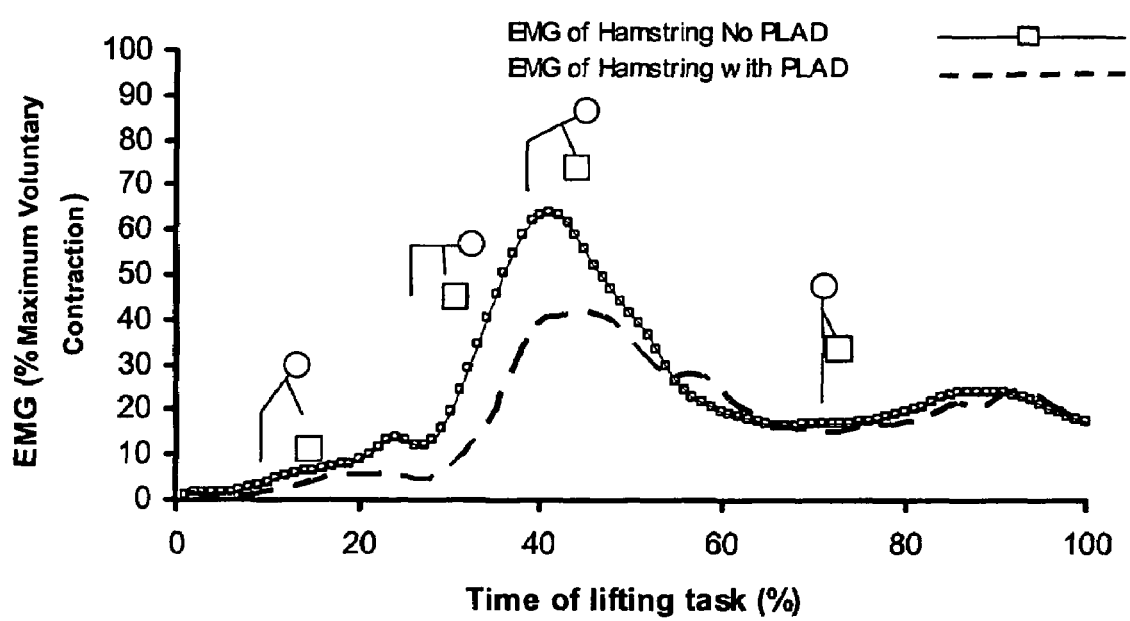
FIG. 20 is a graph showing electromyography of the hamstring of one male subject lifting a 30 kg box with handles, with and without a two elastic member PLAD (described in Example 10), using a stooped position and starting 25 cm from the floor (handle height) and ending at waist height.

Preliminary EMG data were collected from one male subject during a lift of a 30 kg box with handles in a symmetrical lifting technique in a stooped posture with and without a two elastic member PLAD prototype. This two elastic member PLAD had two white Flex-Band® elastics that were each attached between shoulder anchors on a shoulder belt and tibial tuberosity anchors on leg belts and were threaded over a roller bar that was attached to a waist belt at a fulcrum distance "a" of 20 cm (see reference numeral 20 of FIG. 1). The two elastic members were held in distinct channels on the roller bar such that they were kept in line over the left buttock, or in line over the right buttock. The handles were located 25 cm from the bottom of the box, on both sides of the box. The box was lifted from floor to waist height. The study showed a significant reduction of force of hamstring muscles during the lifting task with the PLAD (as shown in FIG. 20). The data suggest that the forces exerted by the hamstring and other posterior hip muscles (e.g., gluteus maximus) close to the hip joint were reduced when PLAD was used. Therefore, PLAD is effective not only for the reduction of moments and forces on L4/L5; but also helps to reduce the moments and forces on the hip.

Equivalents

Although this invention is described in detail with reference to preferred embodiments. thereof, these embodiments are offered to illustrate but not to limit the invention. It is possible to make other embodiments that employ the principles of the invention and that fall within its spirit and scope as defined by the claims appended hereto.

References

Adams, M. A., Hutton, W. C., Stott, J. R. R. (1980) "The resistance to flexion of the lumbar intervertebral joint", *Spine* 3: 245-253.

Abdoli-Eramaki, M., Agnew, M. J., Stevenson, J. M. (2004a) "Integration of electromagnetic tracking systems and virtual reality simulation for 3-D dynamic analyses of spinal loading" Eighth International Symposium on the 3-D Analysis of Human Movement, Tampa, Fla., 2004.

Abdoli-Eramaki, M., Stevenson, J. M. (2004b) "Is an on-body lift assistive device possible?" XVIII Annual International Society for Occupational Ergonomics and Safety Conference," Houston, Tex., 2004.

Abdoli-Eramaki, M., Stevenson, J. M., Agnew, M. J. (2004c) "Recent advantages in validation of the on body Personal Lift Augmentation Device (PLAD),"Windsor, Ontario, Association of Canadian Ergonomists.

Chen, Y. (2003) "The effect of the tightness of abdominal belts on the determination of maximal acceptable weight of lift," *International Journal of Industrial Ergonomics*, 31, 111-117.

Cholewicki, J., McGill, S. M. (1996) "Mechanical stability of the in vivo lumbar spine: Implications for injury and chronic low back pain", *Clin. Biomech.* 11 (1): 1-15.

Dolan, P. and Adams, M. A. (1993) "The relationship between EMG activity and extensor moment generation in the erector spinae muscles during bending and lifting activities," *Journal of Biomechanics*, 26 (4), 513-522.

Guo, H. R., Tanaka, S., Cameron, L. L., Seligman, P. J., Behrens, V. J., Ger, J., Wild, D. K., and Putz-Anderson, V. (1995) "Back pain among workers in the United States: national estimates and workers at high risk," *American Journal of Industrial Medicine*, 28.

Harman, E. A., Rosenstein, R. M., Frykman, P. N. and Nigro, G. A. (1989). "The effects of a weight training belt on blood pressure during exercise," *Journal of Applied Sport Science Research*, 3 (1): 13-18.

Hobson, D. A. (1992) "Comparative effects of posture on pressure and shear at the body-seat interface," *Journal of Rehabilitation Research and Development*, 29(4): 21-31.

Hodges, P. W., Richardson, C. A. (1997) "Feedforward contraction of transversus abdominus is not influenced by the direction of arm movement," *Exp. Brain Res.* 114: 362-370.

Hof, A. T. (1992) "An explicit expression for the moment in multibody systems," *J. Biomech.*, 25: 1209-1211.

Kazerooni, H. (2002) "Human power amplifier for lifting load with slack prevention apparatus," U.S. Pat. No. 6,622, 990.

Kelsey, J. L., Githens, P. B., White, A. A., Holford, T. R., Walter, S. D., O'Connor, T., Ostfeld, A. M., Weil, U., Southwick, W. O., and Calogero, J. A. (1984) "An epidemiologic study of lifting and twisting on the job and risk for acute prolapsed lumbar intervertebral disc," *Journal of Orthopedics*, 2, 61-66.

Kelsey, J. L., White, A. A. (1980) "Epidemiology and impact of low back pain," *Spine,* 5,133-142.

Lavender, S. A., Shakeel, K., Andersson, G. B., and Thomas, J. S. (2000) "Effects of a lifting belt on spine moments and muscle recruitments after unexpected sudden loading," *Spine,* 25(12), 1569-1576.

McGill, S. M. (2002) *Low Back Disorders: Evidence-Based Prevention and Rehabilitation*, Human Kinetics: Champaign, Ill., USA.

McGill, S. M. (1997) "The biomechanics of low back injury: Implications on current practice in industry and the clinic," *J. Biomech.* 30(5): 465-475.

McGill, S. M. (1993) "Abdominal Belts in industry: A position paper on their assets, liabilities and use," *American industrial hygiene association journal,* 54 (12): 752-754.

McGill, S. M., Norman, R. W. (1986) "Partitioning of the L4/L5 dynamic moment into disc, ligamentous and muscular components during lifting." Spine, 11(7): 666-677. NIOSH publication number 94-122 (1994) *Workplace Use of Back Belts*, U.S. Department of Health and Human Services, National Institute for Occupational Safety and Health: Cincinnati, Ohio, USA.

Plamondon, A., Gagnon, M., Desjardins, P. (1996) "Validation of two 3-D segment models to calculate the net reaction forces and moments at the L5/S1 joint in lifting," *Clin. Biomech.* 11 (2): 101-110.

Rafacz, W., McGill, S. M. (1996) "Wearing an abdominal belt increases diastolic blood pressure," *J Occup Environ Med,* 38(9): 925-7.

Shirazi-Adl, A., Ahmed, A. M., and Shrivastava, S. C. (1986) "Mechanical response of a lumbar motion segment in axial torque alone and combined with compression," *Spine,* 11(9)914-927.

Waters, T. R., and Putz-Andersson, V., (1994) "Applications Manual for the revised NIOSH lifting equation," US Department of Health and Human Services, National Institute for Occupational Safety and Health Publication, 94-110.

We claim:

1. A device for supporting and assisting a subject's back during bending and straightening, comprising:
   a shoulder anchor adapted to attach to the shoulders;
   a first leg anchor adapted to attach to a first lower leg and that passes underfoot;
   a second leg anchor adapted to attach to a second lower leg and that passes underfoot;
   at least one member, comprising an elastic member, that connects the shoulder anchor and the first and second leg anchors; and
   a spacer adapted to attach to the subject's waist and extends rearwardly therefrom, the spacer spacing said member away from the subject's back, the spacer not connected to said member;
   wherein the subject's back is supported and assisted during bending and straightening.

2. The device of claim 1, wherein the elastic member is selected from the group consisting of a spring, elastic band, and a combination thereof.

3. The device of claim 1, wherein at least one anchor and/or the spacer is fixed to clothing.

4. The device of claim 1, wherein tension of the elastic member is adjustable.

5. A method for supporting and assisting a subject's back during bending and straightening, comprising:
   attaching a shoulder anchor to the subject's shoulders;
   attaching a first leg anchor to the subject's first lower leg, the first leg anchor passing underfoot;
   attaching a second leg anchor to the subject's second lower leg, the second leg anchor passing underfoot;
   connecting at least one member, comprising an elastic member, to the shoulder anchor and the first and second leg anchors; and
   attaching a spacer to the subject's waist, the spacer extending rearwardly from the subject's back and spacing said member away from the subject's back, the spacer not connected to said member;
   wherein the subject's back is supported and assisted during bending and straightening.

6. The method of claim 5, wherein attaching the anchors and/or the spacer comprises fixing one or more than one anchor and/or the spacer to clothing.

7. The method of claim 5, wherein the elastic member is selected from the group consisting of a spring, elastic band, and a combination thereof.

8. The method of claim 5, further comprising adjusting tension of the elastic member.

* * * * *